United States Patent
Robinson

(10) Patent No.: US 8,998,964 B2
(45) Date of Patent: Apr. 7, 2015

(54) BONE SCREW RETAINING AND REMOVAL SYSTEM

(75) Inventor: James C. Robinson, Atlanta, GA (US)

(73) Assignee: Spectrum Spine, LLC, Atlanta, GA (US)

( * ) Notice: Subject to any disclaimer, the term of this patent is extended or adjusted under 35 U.S.C. 154(b) by 1341 days.

(21) Appl. No.: 12/738,217

(22) PCT Filed: Oct. 16, 2008

(86) PCT No.: PCT/US2008/080213
§ 371 (c)(1),
(2), (4) Date: Jul. 25, 2011

(87) PCT Pub. No.: WO2009/052318
PCT Pub. Date: Apr. 23, 2009

(65) Prior Publication Data
US 2011/0313468 A1    Dec. 22, 2011

Related U.S. Application Data

(60) Provisional application No. 60/980,356, filed on Oct. 16, 2007, provisional application No. 61/029,771, filed on Feb. 19, 2008.

(51) Int. Cl.
*A61B 17/70* (2006.01)
*A61B 17/80* (2006.01)
*A61B 17/92* (2006.01)
*A61B 17/88* (2006.01)

(52) U.S. Cl.
CPC ............. *A61B 17/8042* (2013.01); *A61B 17/92* (2013.01); *A61B 17/8861* (2013.01); *A61B 17/8875* (2013.01)

(58) Field of Classification Search
USPC ......... 606/280, 286, 289, 290, 292, 293, 294, 606/295, 86 B, 99, 104; 81/448, 451, 452; 7/165
See application file for complete search history.

(56) References Cited

U.S. PATENT DOCUMENTS

| | | | | |
|---|---|---|---|---|
| 2,706,506 A | * | 4/1955 | Wagner | 81/453 |
| 3,901,298 A | * | 8/1975 | Eby | 81/455 |
| 6,602,255 B1 | * | 8/2003 | Campbell et al. | 606/290 |
| 6,695,846 B2 | * | 2/2004 | Richelsoph et al. | 606/71 |
| 7,857,839 B2 | * | 12/2010 | Duong et al. | 606/290 |
| 2006/0155285 A1 | | 7/2006 | Anderson | |

FOREIGN PATENT DOCUMENTS

| EP | 1169971 A2 | 1/2002 |
|---|---|---|
| JP | 2005/040600 | 2/2005 |
| WO | WO 00/78238 A1 | 12/2000 |

* cited by examiner

*Primary Examiner* — Anu Ramana
(74) *Attorney, Agent, or Firm* — FisherBroyles, LLP; Anthony J. DoVale

(57) ABSTRACT

A bone screw retention system is provided for a plate which defines a plurality of transversely extending bores that are configured to receive a bone screw for engaging the plate to the cervical spine. One or more retention members, having an elliptical, arcuate, straight, or other shape, can be positioned therein a cavity of the plate such that portions of the retention member(s) extend into a portion of an upper region of each bore to retain a bone screw therein. A bone screw removal device is provided, having at least one tongue member configured to selectively displace the one or more retention members to allow the bone screw to be removed from the respective bore.

23 Claims, 18 Drawing Sheets

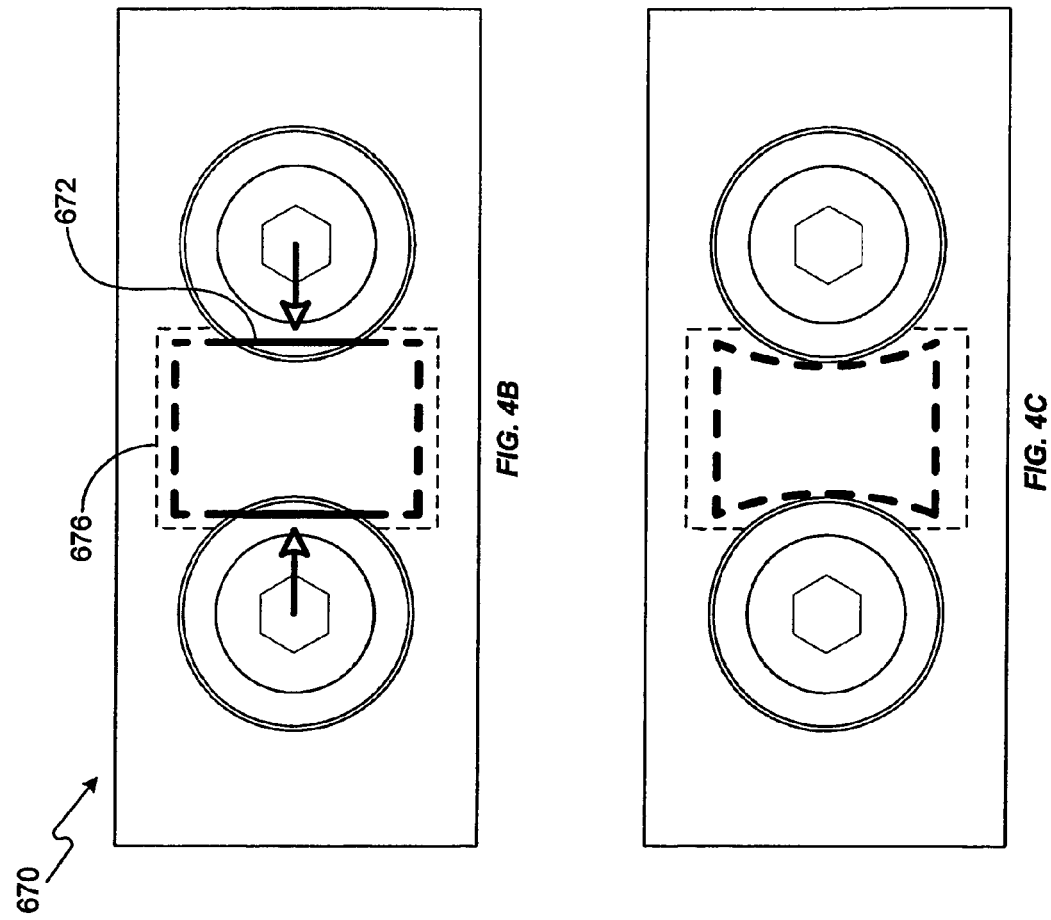
*FIG. 4B*
*FIG. 4C*
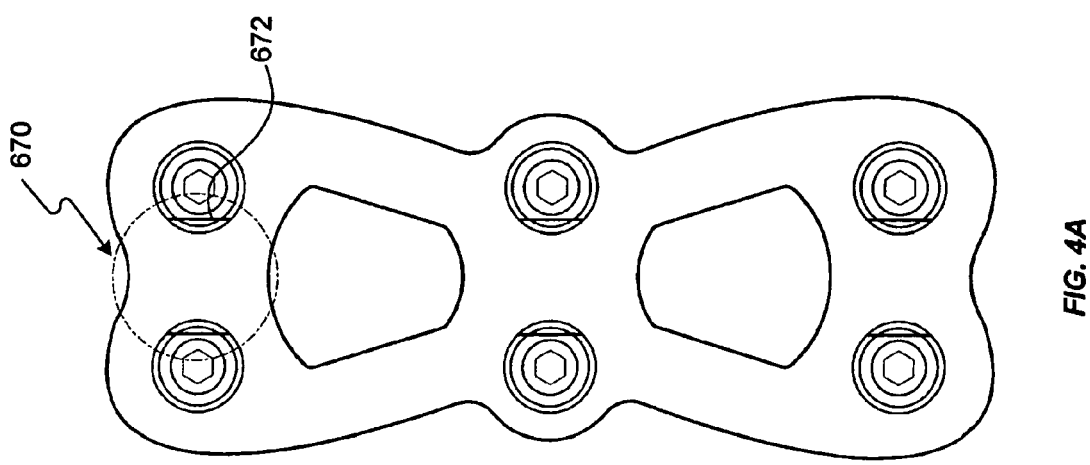
*FIG. 4A*

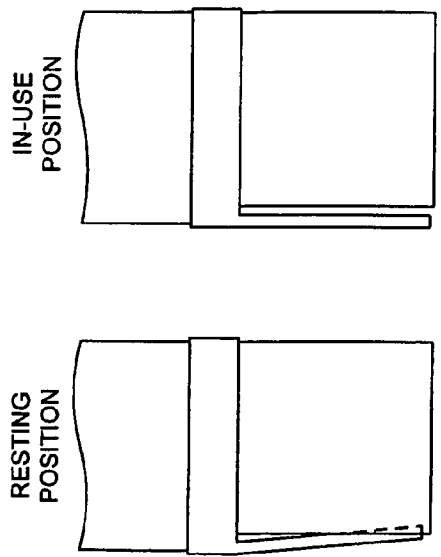
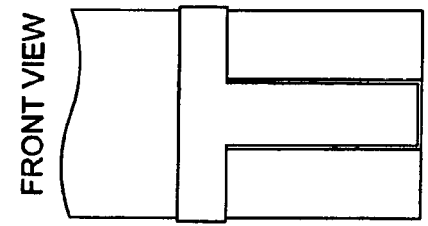
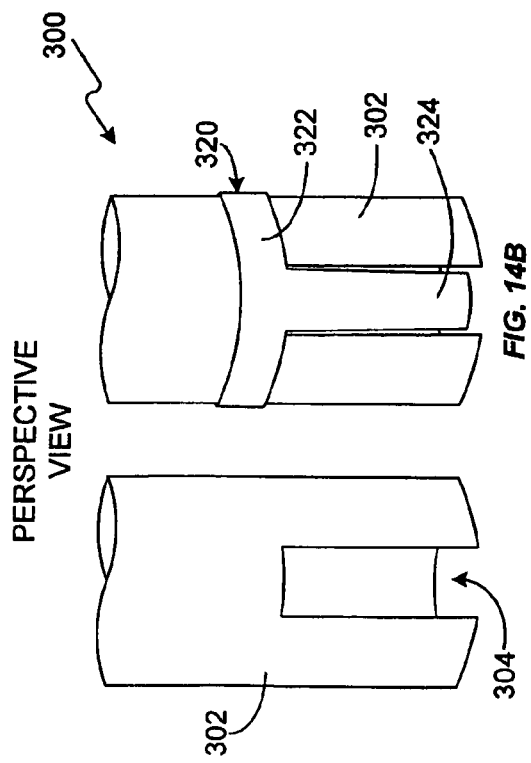

BONE SCREW RETAINING AND REMOVAL SYSTEM

CROSS-REFERENCE TO RELATED APPLICATIONS

This application claims the benefit of U.S. Provisional Application No. 60/980,356, filed on Oct. 16, 2007, and also claims the benefit of U.S. Provisional Application No. 61/029,771 filed on Feb. 19, 2008, both of which applications are herein incorporated by reference in their entirety.

FIELD OF THE INVENTION

The present invention relates generally to surgical procedures, most particularly for use in fixation of the cervical spine. More particularly, the invention pertains to a bone screw retaining system for use in a plating system for use in a system for anteriorly fixating the cervical spine and a removal system for use in removing screws from the plate system.

BACKGROUND OF THE INVENTION

As with any bony structure, the spine is subject to various pathologies that compromise its load bearing and support capabilities. The spine is subject to degenerative diseases, the effects of tumors and, of course, fractures and dislocations attributable to physical trauma. In the past, spinal surgeons have tackled the thorny problems associated with addressing and correcting these pathologies using a wide variety of instrumentation and a broad range of surgical techniques. For example, in spinal surgeries, the fusion of two or more vertebral bodies is required to secure a portion of the spinal column in a desired position. Alternatively, the use of elongated rigid plates has been helpful in the stabilization and fixation of the lower spine, most particularly the thoracic and lumbar spine.

The cervical spine can be approached either anteriorly or posteriorly, depending upon the spinal disorder or pathology to be treated. Many of the well known surgical exposure and fusion techniques of the cervical spine are described in *Spinal Instrumentation*, edited by Drs. Howard An and Jerome Cotler. This text also describes instrumentation that has been developed in recent years for application to the cervical spine, most frequently from an anterior approach.

The anterior approach to achieving fusion of the cervical spine has become the most popular approach. During the early years of cervical spine fusion, the fusions were performed without internal instrumentation, relying instead upon external corrective measures such as prolonged recumbent traction, the use of halo devices or minerva casts, or other external stabilization. However, with the advent of the elongated plate customized for use in the cervical spine, plating systems have become the desired internal stabilization device when performing stabilization operations.

It has been found that many plate designs allow for a uni-corticaly or bi-corticaly intrinsically stable implant. It has also been found that fixation plates can be useful in stabilizing the upper or lower cervical spine in traumatic, degenerative, tumorous or infectious processes. Moreover, these plates provide the additional benefit of allowing simultaneous neural decompression with immediate stability.

During the many years of development of cervical plating systems, particularly for the anterior approach, various needs for such a system have been recognized. For instance, the plate must provide strong mechanical fixation that can control movement of each vertebral motion segment in six degrees of freedom. The plate must also be able to withstand axial loading in continuity with each of the three columns of the spine. The plating system must be able to maintain stress levels below the endurance limits of the material, while at the same time exceeding the strength of the anatomic structures or vertebrae to which the plating system is engaged.

Further plating systems also typically require the thickness of the plate to be small to lower its prominence, particularly in the smaller spaces of the cervical spine. Additionally, the screws used to connect the plate to the vertebrae must not loosen over time or back out from the plate. This requirement, that the bone screws do not loosen over time or back out from the plate, tends to complicate implantation of known plating systems. Such bone screw retention systems generally ensure that the bone screws placed into the vertebrae through the plating system do not back out voluntarily from the plate, but typically do not adequately permit the removal of an associated bone screw when desired by the surgeon.

On the other hand, while the plate must satisfy certain mechanical requirements, it must also satisfy certain anatomic and surgical considerations. For example, the cervical plating system must minimize the intrusion into the patient and reduce the trauma to the surrounding soft tissue. It is known that complications associated with any spinal procedure, and most particularly within the tight confines of cervical procedures, can be very devastating, such as injury to the brain stem, spinal cord or vertebral arteries. It has also been found that optimal plating systems permit the placement of more than one screw in each of the instrumented vertebrae.

More specifically, it is known that bone screws can be supported in a spinal plate in either a rigid or semi-rigid fashion. In a rigid fashion, the bone screws are not permitted any micro-motion or angular movement relative to the plate. In the case of a semi-rigid fixation, the bone screw can move somewhat relative to the plate during the healing process of the spine. It has been suggested that semi-rigid fixation is preferable for the treatment of degenerative diseases of the spine. In cases where a graft is implanted to replace the diseased vertebral body or disk, the presence of a screw capable of some rotation ensures continual loading of the graft. This continual loading avoids stress shielding of the graft, which in turn increases the rate of fusion and incorporation of the graft into the spine.

Similarly, rigid screw fixation is believed to be preferable in the treatment of tumors or trauma to the spine, particularly in the cervical region. It is believed that tumor and trauma conditions are better treated in this way because the rigid placement of the bone screws preserves the neuro-vascular space and provides for immediate stabilization. It can certainly be appreciated in the case of a burst fracture or large tumorous destruction of a vertebra that immediate stabilization and preservation of the vertebral alignment and spacing is essential. On the other hand, the semi-rigid fixation is preferable for degenerative diseases because this type of fixation allows for a dynamic construct. In degenerative conditions, a bone graft is universally utilized to maintain either the disc space and/or the vertebral body itself. In most cases, the graft will settle or be at least partially resorbed into the adjacent bone. A dynamic construct, such as that provided by semi-rigid bone screw fixation, will compensate for this phenomenon.

Furthermore, known plating systems often do not permit sufficient angular freedom for bone screws relative to the plate. Generally, known plating systems have defined bores through which bone screws are placed at a predefined angle. Therefore, the operating surgeon often does not have freedom to insert the bone screws into the vertebrae as to best fit the anatomy of the individual patient. While some known systems do permit bone screw angulation, they typically are not adapted to be used with an easy-to-use bone screw retaining mechanism.

It remains desirable in the art to provide a bone screw retaining system and a bone screw removal device for use with a plating system that addresses the limitations associated with known systems, including but not limited to those limitations discussed above.

SUMMARY OF THE INVENTION

In accordance with the purposes of this invention, as embodied and broadly described herein, this invention, in one aspect, relates to a bone screw retention system that includes an implant having a plate, which defines a plurality of transversely extending bores that are configured to receive a bone screw for engaging the plate to the cervical spine. One or more retention members, having an elliptical, oval, rectangular, square, or other shape, can be positioned therein a cavity of the plate such that portions of the retention member(s) extend into a portion of an upper region of each bore to retain a bone screw therein.

In another aspect, a bone screw removal device is provided, having at least one tongue member configured to selectively displace the one or more retention members to allow the bone screw to be removed from the respective bore. In one aspect, the bone screw removal device includes an outer sleeve having at least one notch extending from a lower surface of the outer sleeve, and an inner sleeve having at least one tongue member that has a protrusion extending from a lower portion of the tongue member. In a further aspect, the inner sleeve is configured to be positioned within the outer sleeve with the tongue member and protrusion of the inner sleeve longitudinally aligned with the notch of the outer sleeve.

In yet another aspect, a method is provided for removing a bone screw from a bone screw retention system utilizing exemplary bone screw removal devices as described herein.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 4A is a top plan view of the exemplary bone screw retention system of FIG. 1A having a respective rectangular dual retention member positioned between a pair of opposing bores of the plate.

FIG. 4B is a partial top plan view of a rectangular dual retention member of FIG. 4A in a first relaxed position in which one side of the rectangular dual retention member extends over a portion of the upper region of a first bore of the plate, and an opposing side extends over a portion of the upper region of a second bore of the plate.

FIG. 4C is a partial top plan view of the rectangular dual retention member of FIG. 4B in a second open position, allowing the first and second bone screws to be removed from the bore.

FIG. 14A is a perspective view of a main sleeve of an exemplary bone screw removal device.

FIG. 14B is a perspective view of an exemplary bone screw removal device, showing a removal sleeve positioned around the main sleeve of FIG. 14A.

FIG. 14C is a front view of the exemplary bone screw removal device of FIG. 14B.

FIG. 14D is a side view of the exemplary bone screw removal device of FIG. 14B, showing a tongue member of the removal sleeve in a first, resting position.

FIG. 14E is a side view of the exemplary bone screw removal device of FIG. 14B, showing the tongue member in a second, in-use position.

DESCRIPTION OF THE PREFERRED EMBODIMENTS

The present invention may be understood more readily by reference to the following detailed description of various embodiments of the invention, examples, figures, and their previous and following description.

Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

As used herein, the singular forms "a," "an" and "the" include plural referents unless the context clearly dictates otherwise. Thus, for example, reference to a "screw" includes aspects having two or more screws unless the context clearly indicates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings:

As used herein, the terms "optional" or "optionally" mean that the subsequently described event or circumstance may or may not occur, and that the description includes instances where said event or circumstance occurs and instances where it does not.

Reference will now be made in detail to various embodiments of the present invention, examples of which are illustrated in the accompanying drawings. Wherever possible, the same reference numbers are used throughout the drawings to refer to the same or like parts.

Figure 1B:
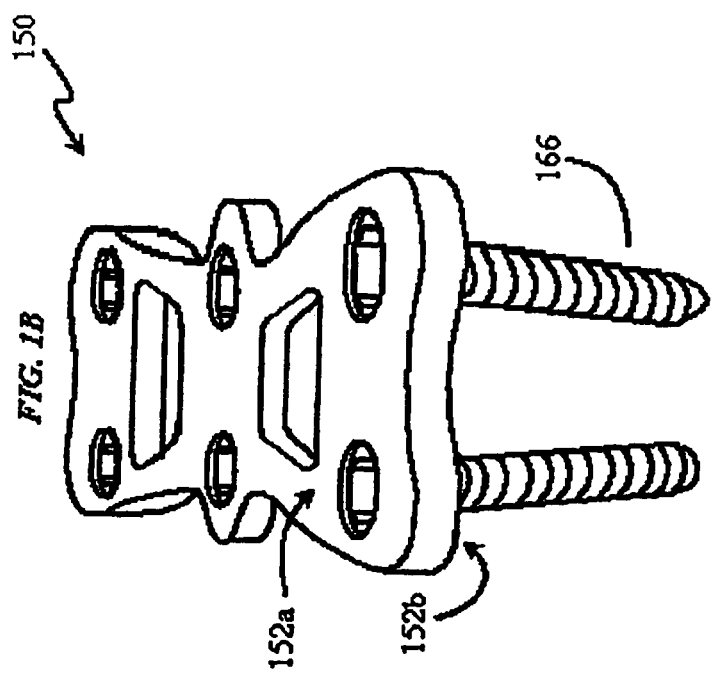
FIG. 1B is a perspective view of the bone screw retention system of FIG. 1A, showing a plurality of bone screws seated therein the bores of the plate and positioned at desired angles relative to the plate.
Figure 1A:
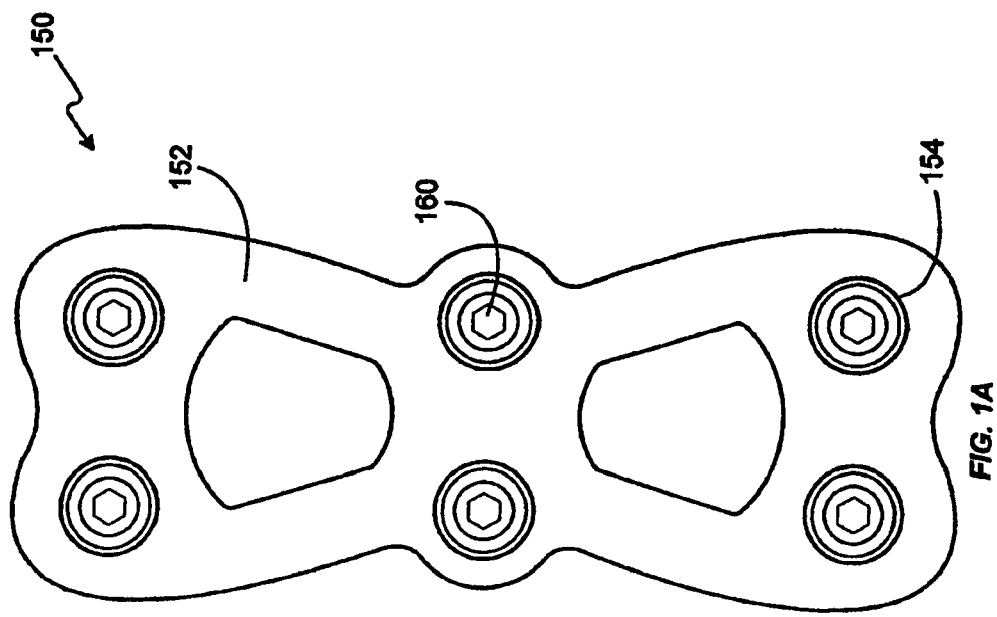
FIG. 1A is a top plan view of an exemplary bone screw retention system comprising a plate having a plurality of bores therein and a plurality of bone screws seated therein the bores.

In one embodiment, and referring to FIGS. 1A and 1B, a plate system can comprise an implant 150, particularly for the spinal column, that can have a joining member, such as a plate 152, that defines a plurality of openings or bores 154, and bone screws 160 capable of being accommodated in the bores. In a further embodiment, at least one retention member is provided and is configured for releasably securing the bone screws therein the bores. The bone screw removal device, in one aspect, provides for the selective removal of the bone screw or screws from the plate at the physician's desire.

In one aspect, the plate 152 defines a plurality of transversely extending bores 154 that are countersunk at a predetermined distance. In one exemplary aspect, a head of a bone screw can be configured to be posteriorly displaceable through a bore of the plate from an anterior surface 152a to a posterior surface 152b of the plate and retained within a portion of the bore between the anterior and posterior surfaces. In one aspect, the plate 152 can have a generally elongated form whose outline generally departs from rectangular due to the presences of partial lobes or lateral projections at the corners and at the center sides of the plate, as can be seen in FIG. 1A. Each partial lobe has a rounded outline and, in an exemplary aspect, can define a respective bore. It is, of course, contemplated that other shapes of the plate can be employed.

Figure 2A:
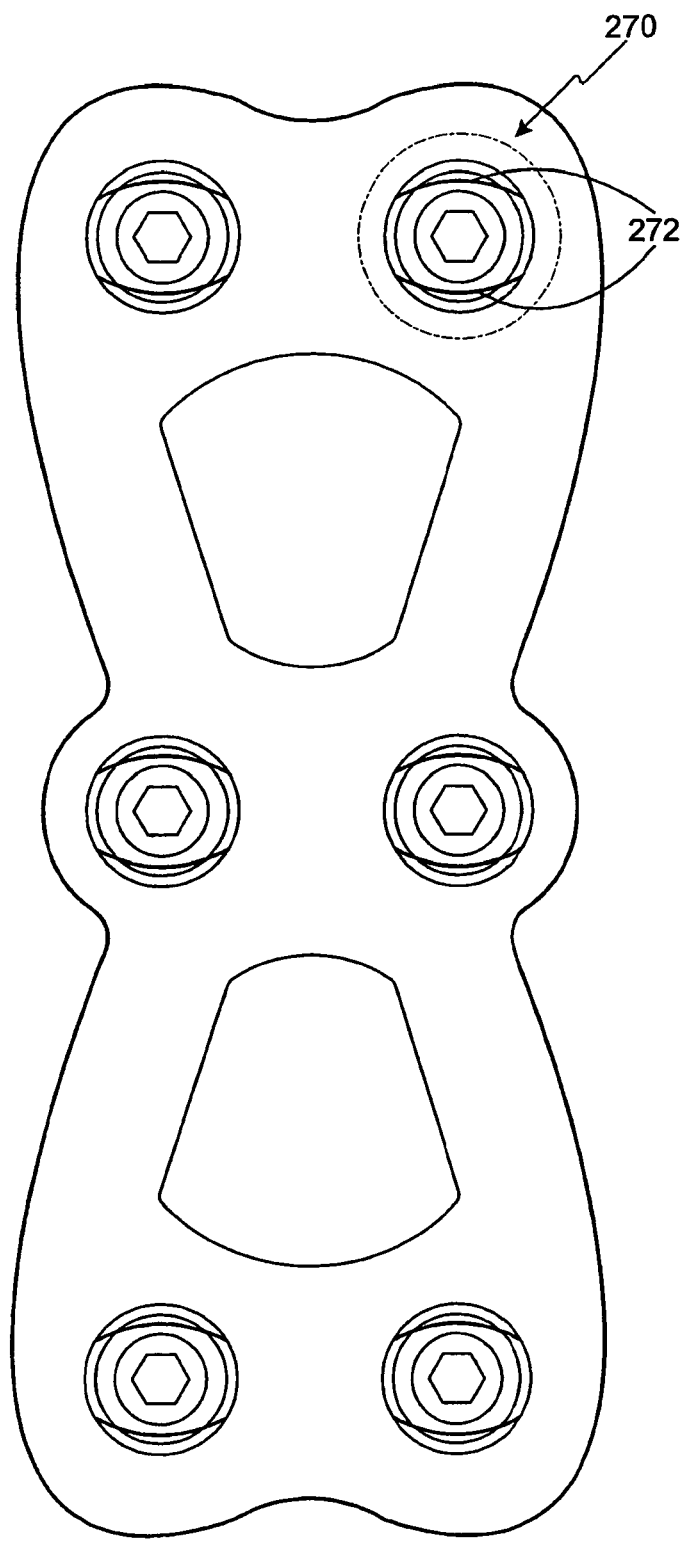
FIG. 2A is a top plan view of the exemplary bone screw retention system of FIG. 1A having a plurality of elliptical ring-shaped retention members.
Figure 2B:
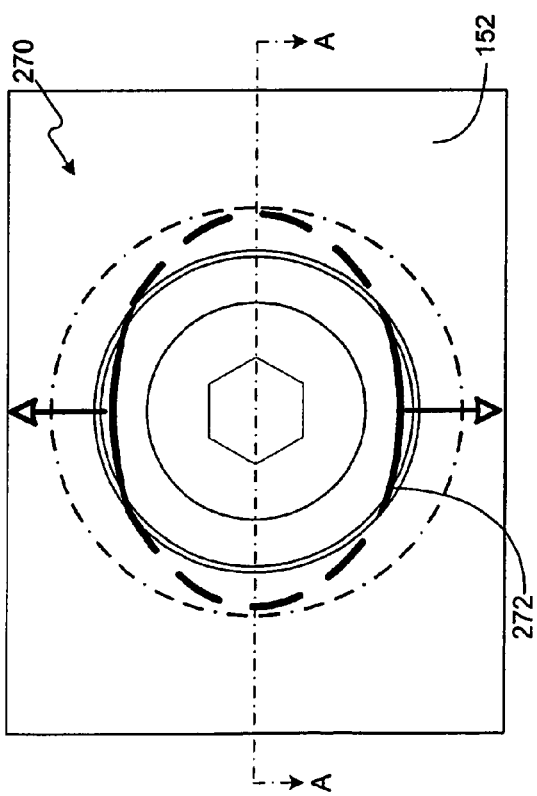
FIG. 2B is a partial top plan view of an elliptical ring-shaped retention member of FIG. 2A in a first relaxed position, in which portions of the retention member extend over a portion of the upper region of a bore of the plate.
Figure 2D:
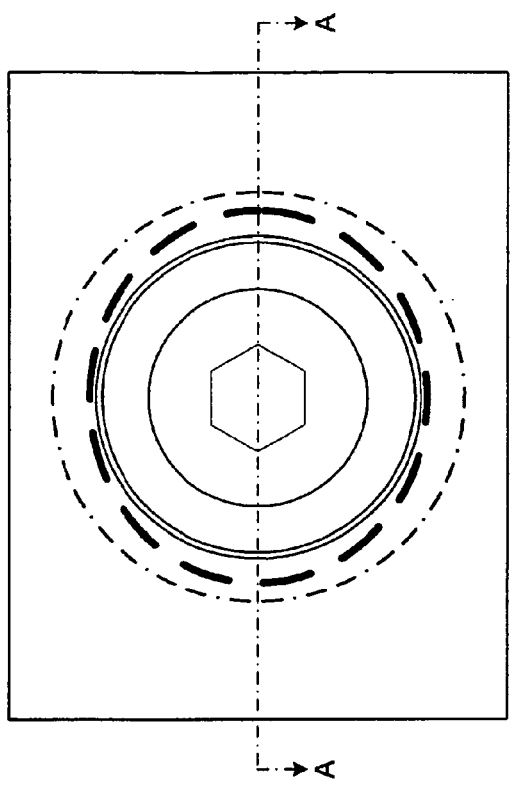
FIG. 2D is a partial top plan view of an elliptical ring-shaped retention member of FIG. 2A in a second open position allowing the bone screw to be removed from the bore.
Figure 2C:
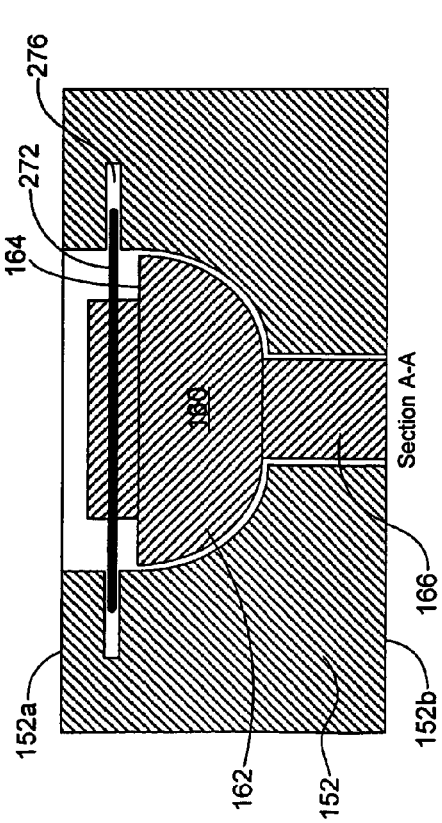
FIG. 2C is a partial side cross-sectional view, taken along line A-A of FIG. 2B, of a bone screw positioned therein a bore of the plate of the bone screw retention system and retained therein by an elliptical ring-shaped retention member in the first relaxed position.
Figure 2E:
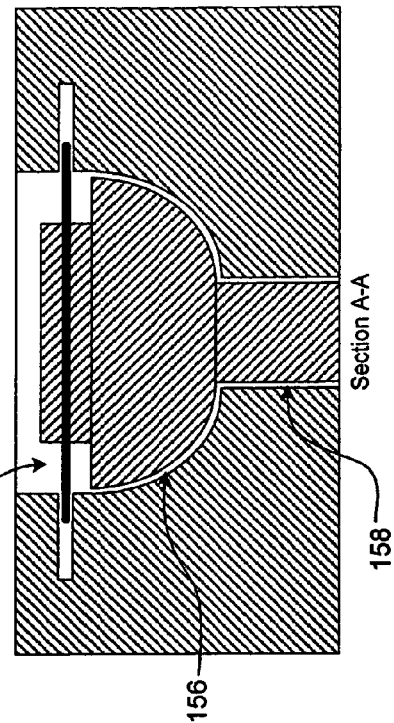
FIG. 2E is a partial side cross-sectional view, taken along line A-A of FIG. 2D, of a bone screw positioned therein a bore of the plate of the bone screw retention system and an elliptical ring-shaped member in the second open position allowing the bone screw to be removed from the bore.

As noted above, the plate 152 defines a plurality of bores 154 that extend substantially transverse therethrough the plate between the anterior and posterior surfaces 152a, 152b of the plate and that are configured for operable receipt of the bone screw(s) 160. In one aspect, the bores extend along a longitudinal axis from the anterior surface to the bottom, bone-contacting, posterior surface 152b of the plate. In one aspect, each bore has an upper region with a first diameter and a lower region that includes a seat 156 for the bone screw and a posteriorly extending tubular shaft 158 that extends to an opening on the posterior surface of the plate, as can be seen in FIG. 2C, for example. In one aspect, the seat of the bore can have at least a partial spherical shape. In another aspect, the plate comprises a plurality of pair opposing bores.

In a further aspect, such as illustrated in FIG. 2C, the bone screw 160 has a head 162 with a maximum diameter that is smaller than the first diameter of the upper region of the bore, which thereby allows the screw head to pass through that region of the bore. In one example, the bone screw can be a conventional self-tapping bone screw. It is, of course, contemplated that conventional non self-tapping bone screws can be used with the system of the present invention. Further, it is contemplated that conventional bone screws with at least partially rotatable heads can be used if a semi-rigid fixation procedure is desired.

According to various aspects, the head 162 of each bone screw 160 can comprise a complementary tapered section that extends from an upwardly facing shoulder surface 164, which is formed by a portion of the head of the bone screw, and tapers toward a threaded shank portion 166 of the bone screw. A portion of the bone screw above the upwardly facing shoulder surface 164 of the bone screw is conventionally configured for operative engagement with a driving tool 150 and has a reduced diameter relative to the diameter of the shoulder of the head of the bone screw.

In one aspect, the tubular shaft 158 of the bore is configured for complementary receipt of the shank of the bone screw such that the bone screw can be fixed at a predetermined angle with respect to the plate. Alternatively, the bone screw can be fixed at an operator selected angle, i.e., be angularly displaceable. In one aspect, the tapered section of the bone screw can be configured for complementary rotatable contact with an exemplary spherically shaped seat of the bore. It is contemplated that the tapered section of the bone screw can be substantially linear or, optionally, substantially hemispherical. Further, the shank of the bone screw can be threaded in any well known fashion and may include an axial groove to enable the bone screw to be self-boring and self-tapping.

In another aspect, the shaft 158 of the bore can have an operative diameter that is greater than the diameter of the shank 166 of the bone screw intermediate the head of the bone screw and its distal end. As a result, the bone screw 160 is angularly displaceable within the shaft of the bore between the seat and the posterior surface opening. The bone screw can thus be tilted within the shaft of the bore relative to the longitudinal axis of the bore to facilitate positioning the bone screw at a desired location in the bone by advancing the threaded shank portion of the bone screw within the bone at an angle relative to the posterior surface 152b of the plate. In one aspect, the bone screw 160 can be angularly displaced relative to the longitudinal axis of the bore up to an angle of about 20 degrees. Thus, the physician or surgeon has, at his disposal, the freedom to orient the bone screw angularly with respect to the joining member or plate, which allows him to optimize the anchorage. In one aspect, the bone screw(s) can be rotatably mounted therein the underlying bone tissue using a conventional screw driver, a drive socket, and the like.

According to various embodiments, a retaining system is provided that is configured to secure a bone screw therein a respective bore. In one aspect, the retaining system comprises at least one elastically deformable retention member. In another aspect, the retention member can have an edge portion. In this aspect, at least a portion of the at least one retention member can be positioned therein each at least one cavity of the plate such that portions of the at least one retention member extend into an upper region of each of the bores. In a further aspect, the at least one retention member can be configured to mount therein the at least one cavity and can be configured to be movable between a first relaxed position and a second compressed position. In a further aspect, the at least one elastically deformable retention member can comprise a plurality of elastically deformable retention members.

In the first relaxed position, a portion of the edge portion of the at least one retention member extends inwardly substantially transverse to and toward the longitudinal axis of the respective bore and into the upper region of the bore. As one will appreciate, an effective inner diameter of the upper region of the bore is decreased in the first relaxed position. In another aspect, a portion of the edge portion of the at least one retention member extends over portions of the upper region of a plurality of bores of the plate in the first relaxed position.

In the second compressed position, portions of the at least one retention member are medially biased outwardly away from the longitudinal axis of the bore towards an outer wall of the upper region of the bore, which increases the effective inner diameter of the upper region of the bore. Thus, it is contemplated that the illustrate embodiments provides a means for engaging portions of the edge portion of the at least one retention member thereby medially biasing portions of the at least one retention member away from the longitudinal axis of the bore towards an outer wall of the upper region of the bore increasing the effective inner diameter of the upper region of the bore.

In one aspect, the retention system can comprise at least one retention member having an outer edge. In another aspect, the at least one retention member can be a resilient, continuous, ring-shaped member in the first relaxed position. As can be appreciated, the at least one resilient retention member can have spring constant $K_R$. As also can be appreciated, it is contemplated that the at least one continuous ring-shaped member can be circular, oval, elliptical, square, rectangular, or any other continuous geometric shape.

In one embodiment, a first retention mechanism 270 is provided that comprises a ring-shaped retention member 272, such as illustrated in FIGS. 2A-2E. The ring-shaped retention member, in one aspect, is substantially elliptical in its relaxed position, such as shown in the top plan view of FIG. 2B. The first retention mechanism 270, in one aspect, comprises a cavity 276 formed therein the plate 152, which is configured for receiving the ring-shaped retention member 272. The cavity can be substantially planar and substantially circular in the plane (illustrated in FIG. 2B) and can define a plane that is substantially parallel to the anterior surface 152a of the plate. The cavity can be formed to extend inwardly into the plate from an upper portion of the bore 154, above the seat 156 of the bore, such as shown in FIG. 2C. Thus, when a retention member is inserted therein the cavity, and a bone screw 160 is operatively placed therein the bore, the retention member is positioned proximate, but above the upwardly facing shoulder 164 of the bone screw.

When a bone screw 160 is positioned therein the bore 154, portions of the retention member 272 will extend across portions of the shoulder 164 of the bone screw, thereby preventing the bone screw from unseating or backing out of the bore. It is contemplated that the ring-shaped retention member will be of a selected shape such that it will remain in this relaxed, retaining position absent any shear or lateral forces being applied to it. To access the bore (i.e., to insert or remove a bone screw), a physician can use a driver/removal tool in combination with a bone screw removal device (as described further herein below) to flex the retention member 272 into a more rounded, open position. For example, as shown in FIGS. 2B and 2D, the portions of the ring-shaped retention member that extend across the shoulder 164 of the bone screw can be flexed or forced outwardly toward the cavity 276 until they no longer extend across the shoulder of the bone screw. One skilled in the art will appreciate that, when the retention member is biased into the open position (FIGS. 2D and 2E), the bone screw can be removed. In a further aspect, it is contemplated that means can be provided to prevent the ring-shaped retention member from rotating within the cavity, particularly when it is being flexed to access the bone screw.

Figure 3B:
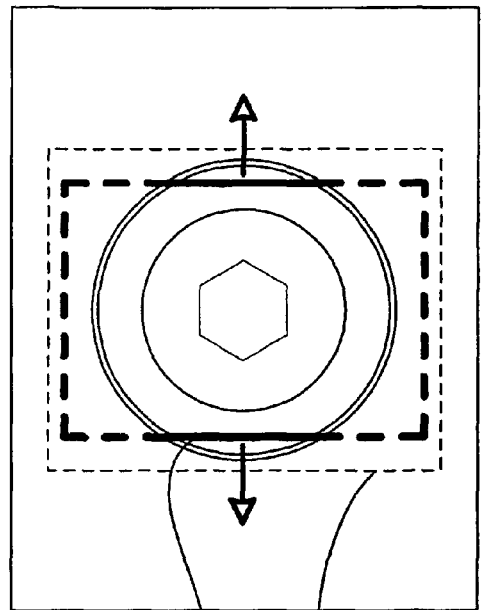
FIG. 3B is a partial top plan view of a rectangular retention member of FIG. 3A in a first relaxed position in which two sides of the rectangular retention member extend over a portion of the upper region of a bore of the plate.
Figure 3C:
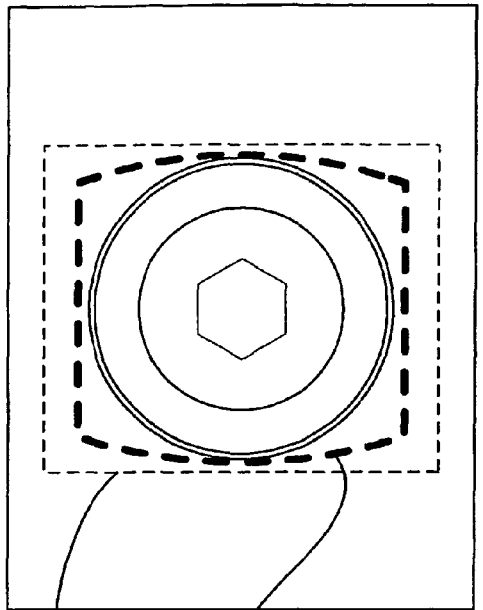
FIG. 3C is a partial top plan view of the rectangular retention member of FIG. 3B in a second open position, allowing the bone screw to be removed from the bore.
Figure 3A:
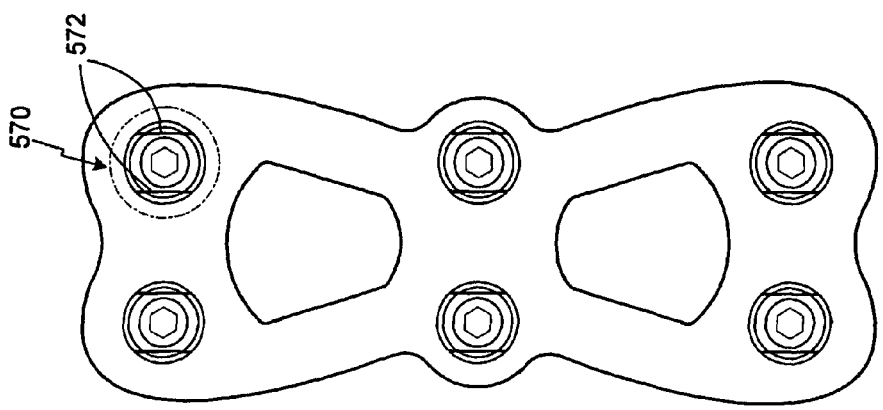
FIG. 3A is a top plan view of the exemplary bone screw retention system of FIG. 1A having a respective rectangular retention member positioned therein each of the bores of the plate.

In another embodiment, a second retention mechanism 570 is provided that comprises a substantially rectangular retention member 572 having, in a first relaxed position, four substantially straight sides, such as illustrated in FIGS. 3A-3C. At least one side of the rectangular retention mechanism, in its relaxed (unstressed) positions, can extend across a portion of the shoulder of a respective bone screw. In a further aspect, two opposing sides of the rectangular retention mechanism can extend across portions of the shoulder of the respective bone screw, such as shown in FIG. 3B. In order to access the bone screw, the opposing sides can be flexed or stressed outwardly into an arcuate shape until the bone screw is unobstructed, such as shown in FIG. 3C. It is contemplated that the other two opposing sides will be drawn toward each other and can remain substantially straight as the retaining sides are bowed outwardly. A cavity 576 can be formed therein the plate to receive and retain the rectangular retention member. The cavity can be substantially planar in a plane that is substantially parallel to the anterior surface of the plate. The cavity can be formed to extend inwardly into the plate from an upper portion of the bore, above the seat of the bore. Such a cavity can be similar to that shown in FIG. 2C, although it can be sized and shaped (i.e., rectangular, circular, etc.) to receive and accommodate the rectangular retention member in its first relaxed position and second stressed or flexed position.

According to another aspect, a third retention mechanism 670 is provided that comprises a rectangular dual retention member 672, such as illustrated in FIGS. 4A-4C. In one aspect, the dual retention member is configured to be positioned between opposing bores. Opposing sides of the retention member are configured to extend across portions of the opposing bores. For example, as illustrated in FIG. 4B, in one aspect, a first side extends across a portion of a first bore, and a second, opposing side extends across a portion of a second bore. Thus, it is contemplated that a single rectangular dual retention member 672 can be used to secure at least two bone screws therein respective bores. In their first, relaxed position, the first and second sides of the retention member extend across the bores to retain the bone screws therein. In order to access the bone screw, the first and second sides can be flexed or stressed inwardly into an arcuate shape until the respective bone screws are unobstructed, such as shown in FIG. 4C. As the first and second sides are flexed inwardly, it is contemplated that the other sides will be drawn toward each other and can remain substantially straight. A cavity 676, such as that shown in FIGS. 4B and 4C can be formed therein the plate to receive and retain the rectangular dual retention member 672. As may be appreciated, the cavity can be sized and shaped to receive and retain the retention member. Additionally, it is contemplated that the at least one elastically deformable retention member can be positioned therein each at least one cavity such that a center of the at least one retention member is substantially stationary geometrically when the at least one retention member is in the first relaxed position and the second compressed position.

According to various aspects of the present invention, a bone screw removal device is provided for removing bone screw(s) from a bone screw retention system, such as the exemplary bone screw retention systems described herein. If desired and as may be appreciated, the bone screw removal device can also be used to insert a bone screw into a bone screw retention system.

Figure 5B:
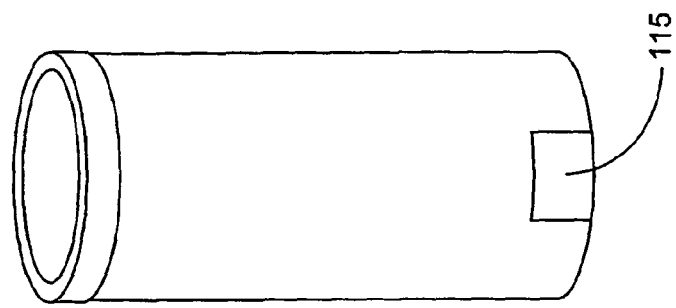
FIG. 5B are perspective views of a bone screw removal device showing, from left to right, the inner sleeve of FIG. 5A positioned within an outer sleeve, the inner sleeve in a first raised position with a tongue member of the inner sleeve retained within the outer sleeve; and the inner sleeve in a second, lowered position with a tongue member protrusion of the inner sleeve extending into a notch of the outer sleeve.
Figure 5A:
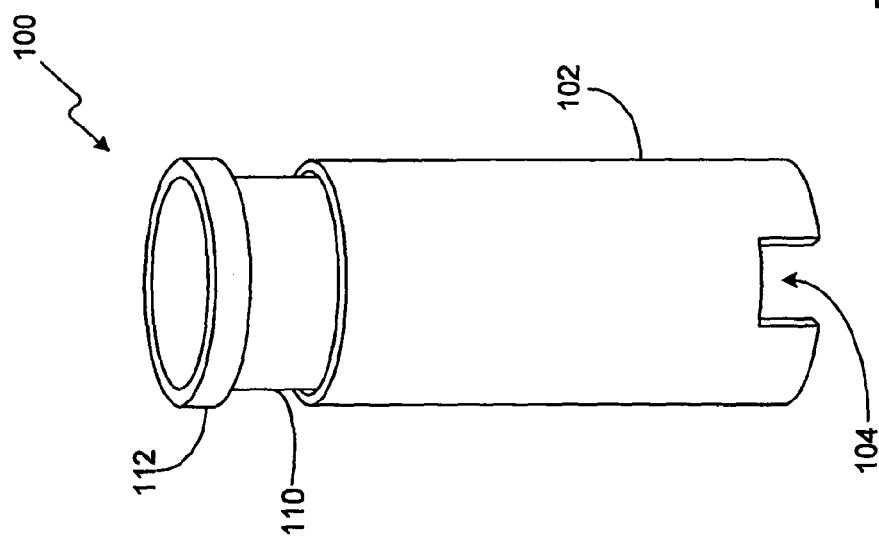
FIG. 5A is a perspective view of an inner sleeve of a bone screw removal device.
Figure 5A:
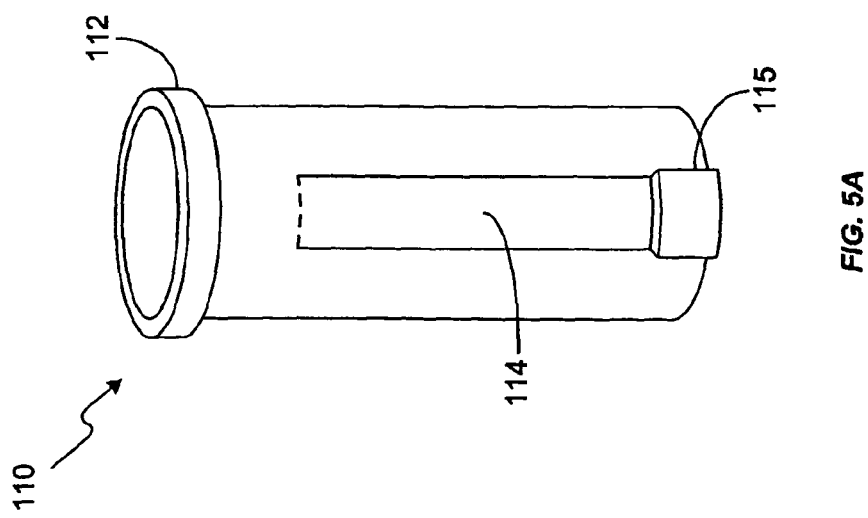
Figure 6:
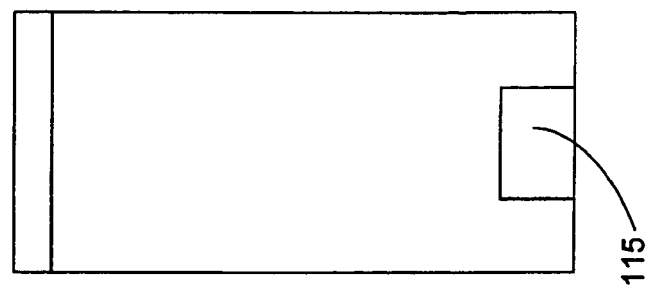
FIG. 6 are front elevational views of, from left to right, the inner sleeve of the bone screw removal device of FIG. 5A; the inner sleeve positioned within the outer sleeve in the first, raised position; and the inner sleeve in the second, lowered position with the tongue member of the inner sleeve extending into the notch of the outer sleeve.
Figure 6:
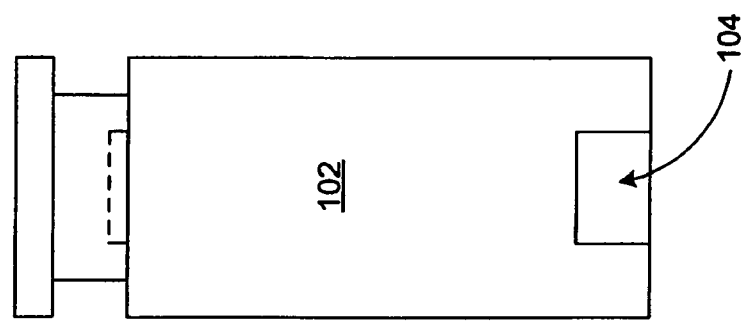
Figure 6:
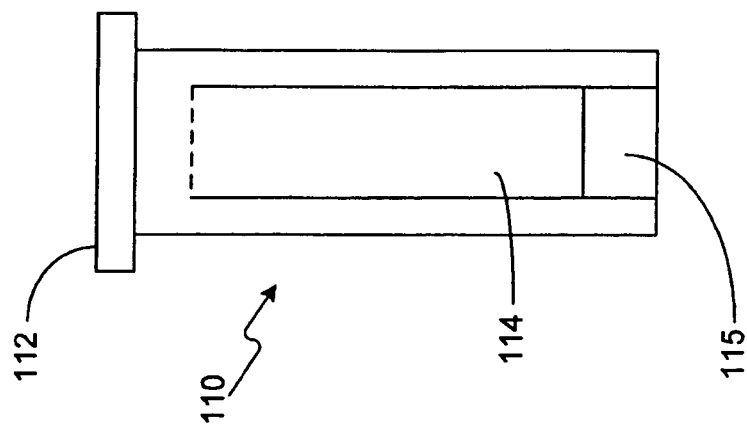

A bone screw removal device 100 according to one aspect comprises an outer sleeve and an inner sleeve sized and shaped to be received within the outer sleeve. In one aspect, the outer sleeve 102 comprises a substantially cylindrical and hollow body, such as shown in FIG. 5B, that has an upper end and an opposing lower end. An inner sleeve 110 can have a substantially cylindrical, hollow body with a respective upper end and an opposing lower end. The inner sleeve defines a conduit therein the body. A flange 112 can be provided at the upper end of the inner sleeve, the flange having a larger diameter than the diameter of the cylindrical body, such as illustrated in FIG. 5A. It is contemplated that the inner diameter of the outer sleeve is greater than the outer diameter of the inner sleeve.

An inner sleeve 110, in one aspect, has a resilient tongue member 114 that extends longitudinally down a portion of the body of the inner sleeve. In one aspect, an upper portion of the tongue member is defined by a portion of the body of the inner sleeve. In a further aspect, the upper portion of the tongue member can be spaced at a predetermined distance from the flange 112, such as illustrated in FIG. 5A. As can be appreciated, the tongue member can be a leaf spring having a spring constant $K_T$. A lower portion of the tongue member 114 can further comprise a protrusion 115 that extends outwardly from the lower portion. In one aspect, the protrusion can be generally rectangular in shape; optionally and without limitation, the protrusion can be any other shape, such as semi-circular, partially circular, semi-elliptical, partially elliptical, triangular, or other shape.

Figure 7A:
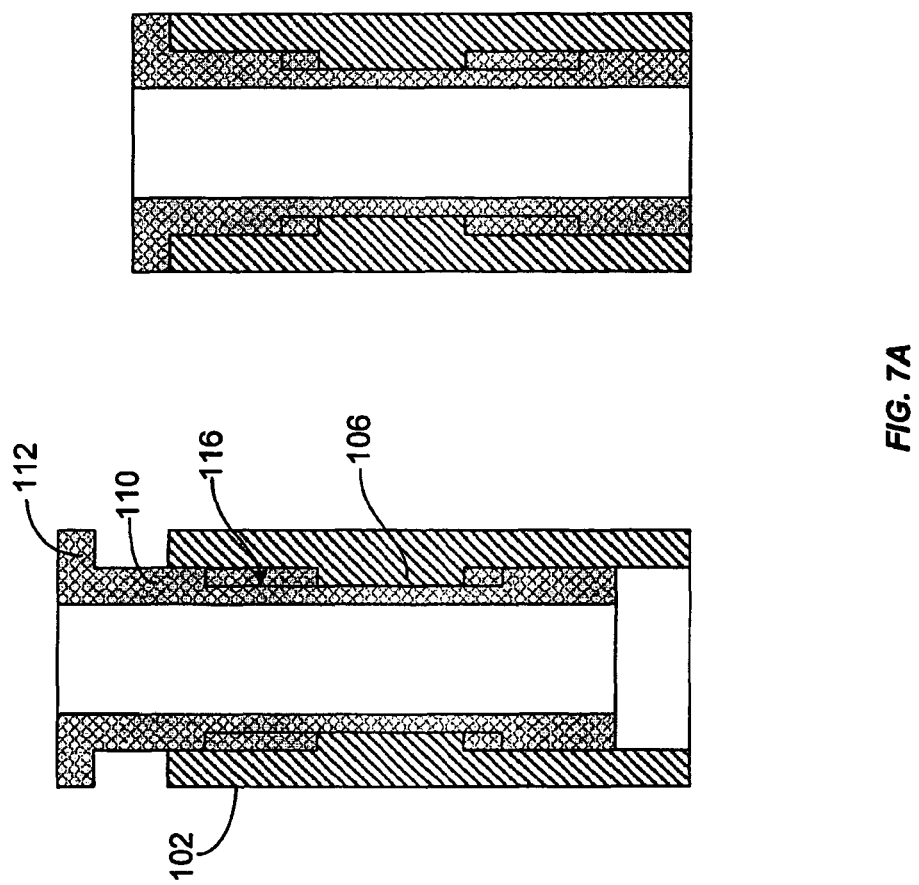
FIG. 7A are front cross-sectional views of the bone screw removal device showing the inner sleeve in the first, raised position (shown on the left) and the second, lowered position (shown on the right).
Figure 7B:
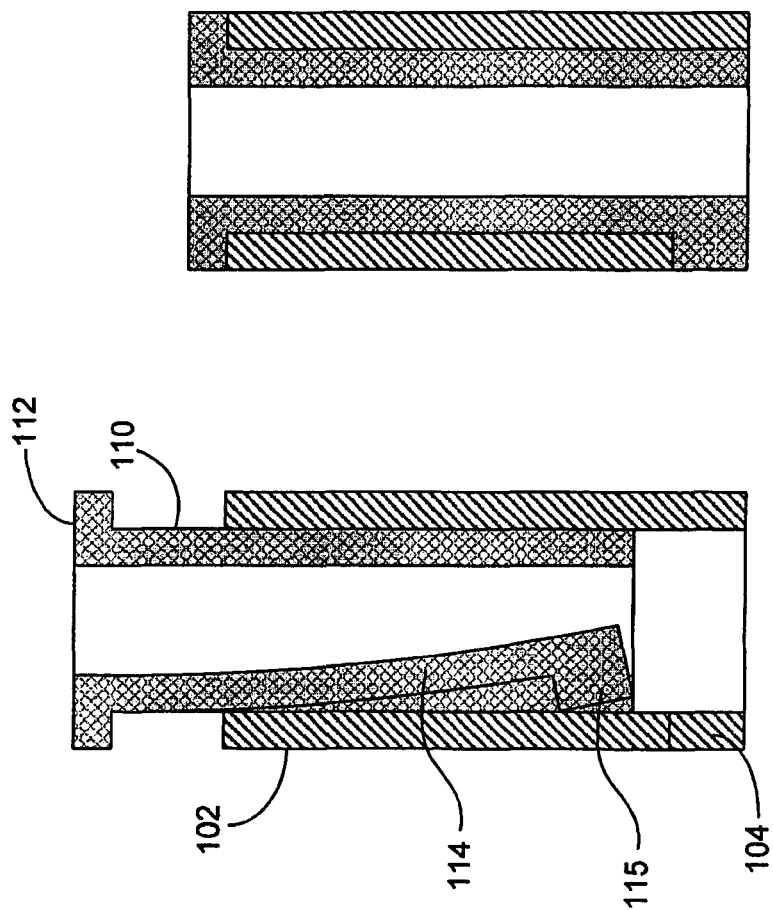
FIG. 7B are side cross-sectional views of the bone screw removal device showing the inner sleeve in the first, raised position (shown on the left) and the second, lowered position (shown on the right).
Figure 7C:
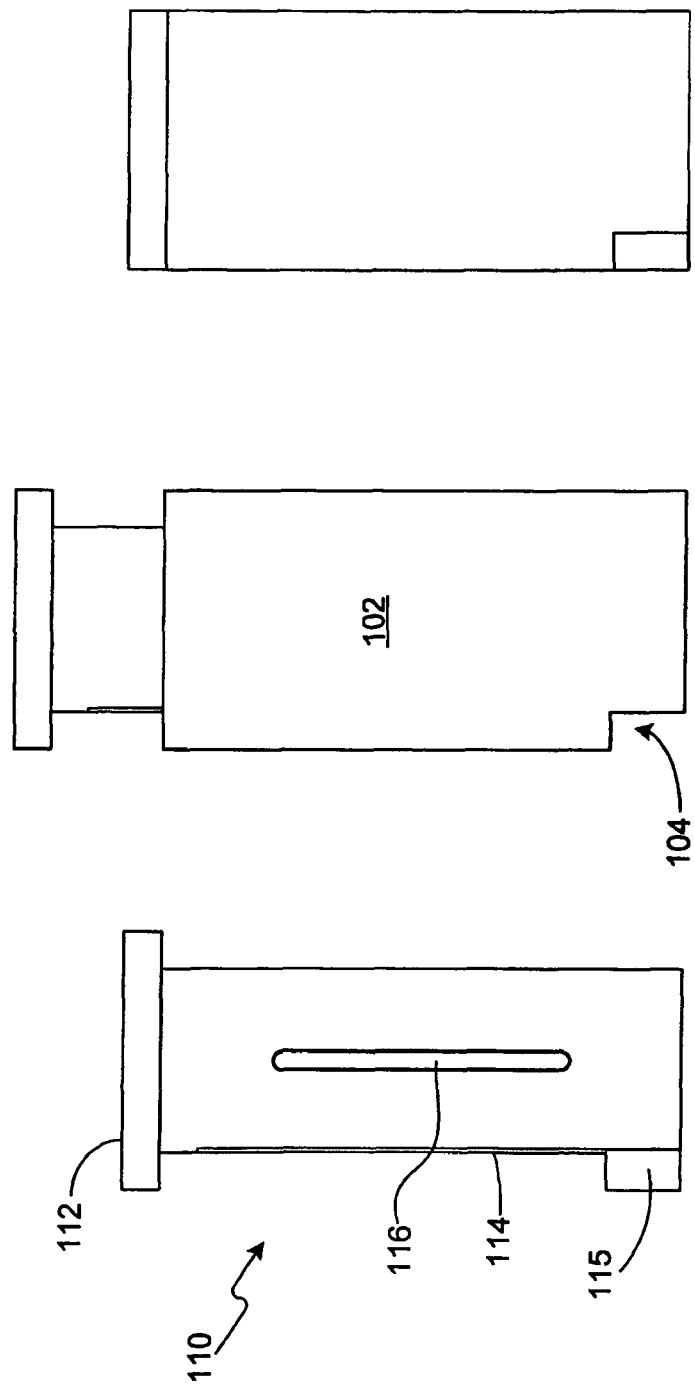
FIG. 7C are side elevational views of, from left to right, the inner sleeve of the bone screw removal device of FIG. 5A, showing the guide slot formed therein the side of the inner sleeve; the inner sleeve positioned within the outer sleeve in the first, raised position; and the inner sleeve in the second, lowered position with the tongue member of the inner sleeve extending into the notch of the outer sleeve.

According to a further aspect, one or more longitudinal guide slots 116 can be formed in a portion of the body of the inner sleeve 110, such as shown in FIGS. 7A and 7C. Thus, the guide slot(s) can be formed substantially parallel to a longitudinal axis of the substantially cylindrical body of the inner sleeve. In a particular aspect, a pair of opposing longitudinal guide slots can be formed in the body, such that they are positioned approximately 180 degrees apart within the body of the inner sleeve. In a further aspect, the guide slots can be respectively positioned approximately 90 degrees from the center of the tongue member. The guide slots can be formed as open slots that extend fully through the side wall of the inner sleeve. Optionally, the guide slots 116 can be of a predetermined depth and do not extend fully through the side wall, such as shown in FIG. 7A. In yet a further aspect, the guide slots can extend longitudinally for a predetermined distance along the body, the predetermined distance being less than the total height of the body. Thus, as shown in FIGS. 7A and 7C, the guide slot(s) 116 can begin at a spaced distance from the flange 112 and extend longitudinally to a spaced distance from the lower edge of the inner sleeve. As will be explained further below, the guide slot(s) are configured to receive a projection 106 of the outer sleeve 102.

One or more openings, or notches, 104 can be defined in the lower end of the outer sleeve. In one aspect, the opening can be a substantially rectangular notch, such as shown in FIG. 5B. Optionally, the notch can be semi-circular, partially circular, semi-elliptical, partially elliptical, triangular, or any other shape. In a further aspect, the notch 104 can be sized and shaped to receive at least a portion of the protrusion 115 of the tongue member 114. Thus, in one exemplary aspect, the protrusion can be substantially rectangular and the notch has a complementary rectangular shape to operatively receive the protrusion.

The outer sleeve 102 can further comprise longitudinal projections 106 that extend inwardly from the inner wall of the outer sleeve. In one aspect, the projections are substantially parallel to the longitudinal axis of the substantially cylindrical outer sleeve. The projections can be positioned approximately 180 degrees from each other along the inner wall of the outer sleeve. In a further aspect, the projections can be respectively positioned approximately 90 degrees from, on either side of, the center of the notch 104. The projections, in one aspect, extend only partially along the inner wall of the outer sleeve. Thus, as illustrated in FIG. 7A for example, the projection(s) 106 can begin at a spaced distance from an upper edge of the outer sleeve, and can end at a spaced distance from a lower edge of the outer sleeve. In one aspect, the length of each of the projections 106 is less than the length of the guide slots 116 of the inner sleeve. The projections can be, for example, from 25 to 75% of the length of the guide slots. It is contemplated that the projections are sized, shaped and positioned to be received by the guide slots of the inner sleeve.

Figures 8A, 8B:
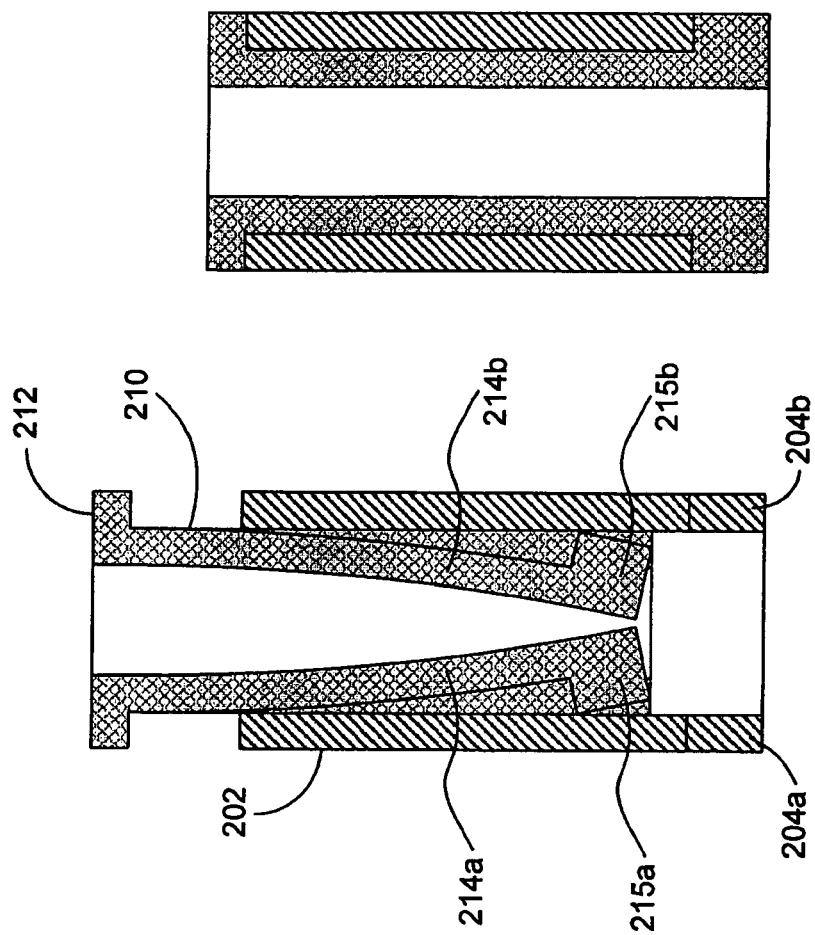
FIG. 8A is a side cross-sectional view of a bone screw removal device showing an inner sleeve having a pair of opposing tongue members, the inner sleeve positioned within an outer sleeve in a first, raised position.
FIG. 8B is a side cross-sectional view of the bone screw removal device of FIG. 8A showing the inner sleeve positioned within the outer sleeve in a second, lowered position.
Figure 8C:
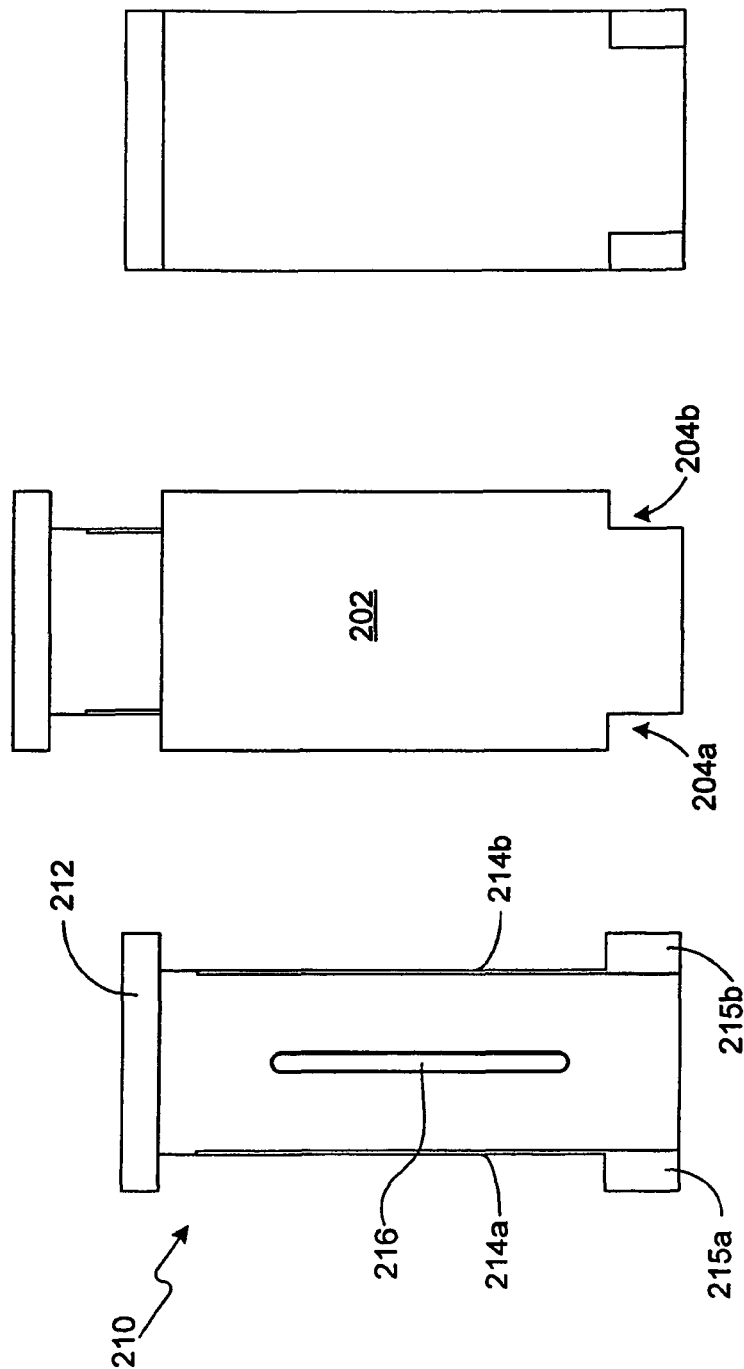
FIG. 8C are side elevation views of, from left to right, the inner sleeve of the bone screw removal device of FIG. 8A showing the pair of opposing tongue members and a guide slot formed therein the side of the inner sleeve; the inner sleeve positioned within the outer sleeve in the first, raised position; and the inner sleeve in the second, lowered position with tongue member protrusions of the inner sleeve extending into respective notches of the outer sleeve.

As may be appreciated, in various aspects, a single retention member can be provided within each bore to retain a bone screw therein. Optionally, two or more retention members can be provided to retain a bone screw therein a respective bore. Similarly, bone screw removal devices can be provided that have the ability to displace single retention members, as well as dual (or more) retention members. For example, in a bone screw retention system in which a single retention member is used to retain each bone screw, a bone screw removal device having a single tongue member and protrusion, such as shown in FIGS. 5A-5B, 6, and 7A-7C, can be provided. Optionally, a dual bone screw removal device (i.e., having dual opposing tongue members) such as shown in FIGS. 8A-8C can be provided, although it is contemplated that only one tongue member will be needed to displace the single retention mechanism. Likewise, in a bone screw retention system having two or more retention members retaining each bone screw, a bone screw removal device having at least two tongue members can be provided.

In use, the inner sleeve 110 is positioned therein the outer sleeve 102 with the projections 106 inserted into respective guide slots 116 such that the tongue member 114 and protrusion 115 are longitudinally aligned with the notch 104 of the outer sleeve. As illustrated in FIG. 7A, in one aspect, the projections are formed within the outer sleeve at a predetermined position to allow the inner sleeve to move from and between a first position in which the flange 112 is spaced from the upper edge of the outer sleeve (FIG. 7A, left), to a second position in which the flange substantially abuts the upper edge of the outer sleeve (FIG. 7A, right). As may be appreciated, when in the first compressed position, the tongue member 114 is pushed inwardly toward the inner portion of the inner sleeve, such as shown in FIG. 7B, due to the presence of the protrusion 115 at the distal end of the tongue member. As the inner sleeve is moved toward and to the second relaxed position, the resilient forces of the tongue member can urge the protrusion to extend into the notch 104 of the outer sleeve 102. In one aspect and as shown in the figures, in the second relaxed position, the at least one protrusion engages an outer edge of the edge portion of the at least one retention member of the retaining system. Optionally, in the second relaxed position, the at least one protrusion engages an inner edge of the edge portion of the at least one retention member.

Figure 9:
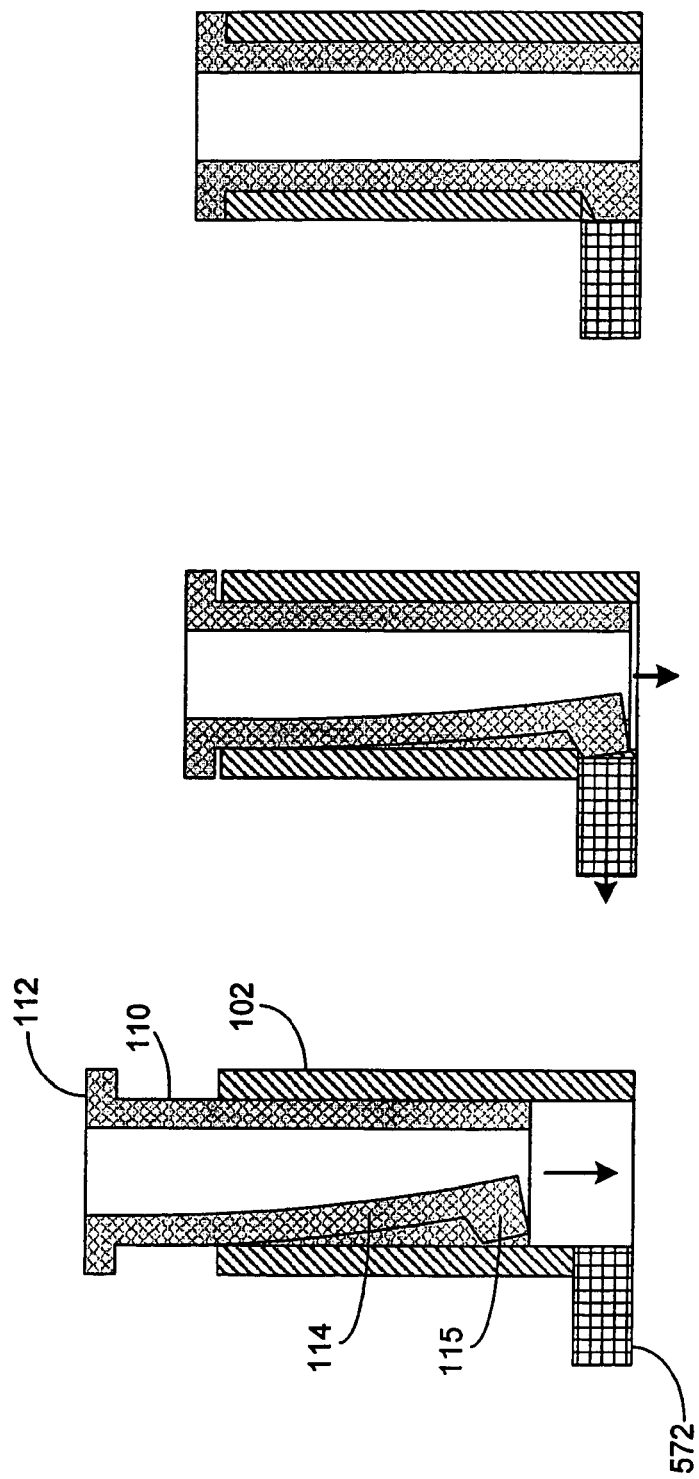
FIG. 9 illustrate exemplary downward movement of an inner sleeve within an outer sleeve, the tongue member protrusion of the inner sleeve extending therethrough the notch of the outer sleeve and pushing out a retention member as the inner sleeve is lowered from a first raised position (shown on the left), through an intermediate position (middle) to a second lowered position (shown on the right).
Figure 10:
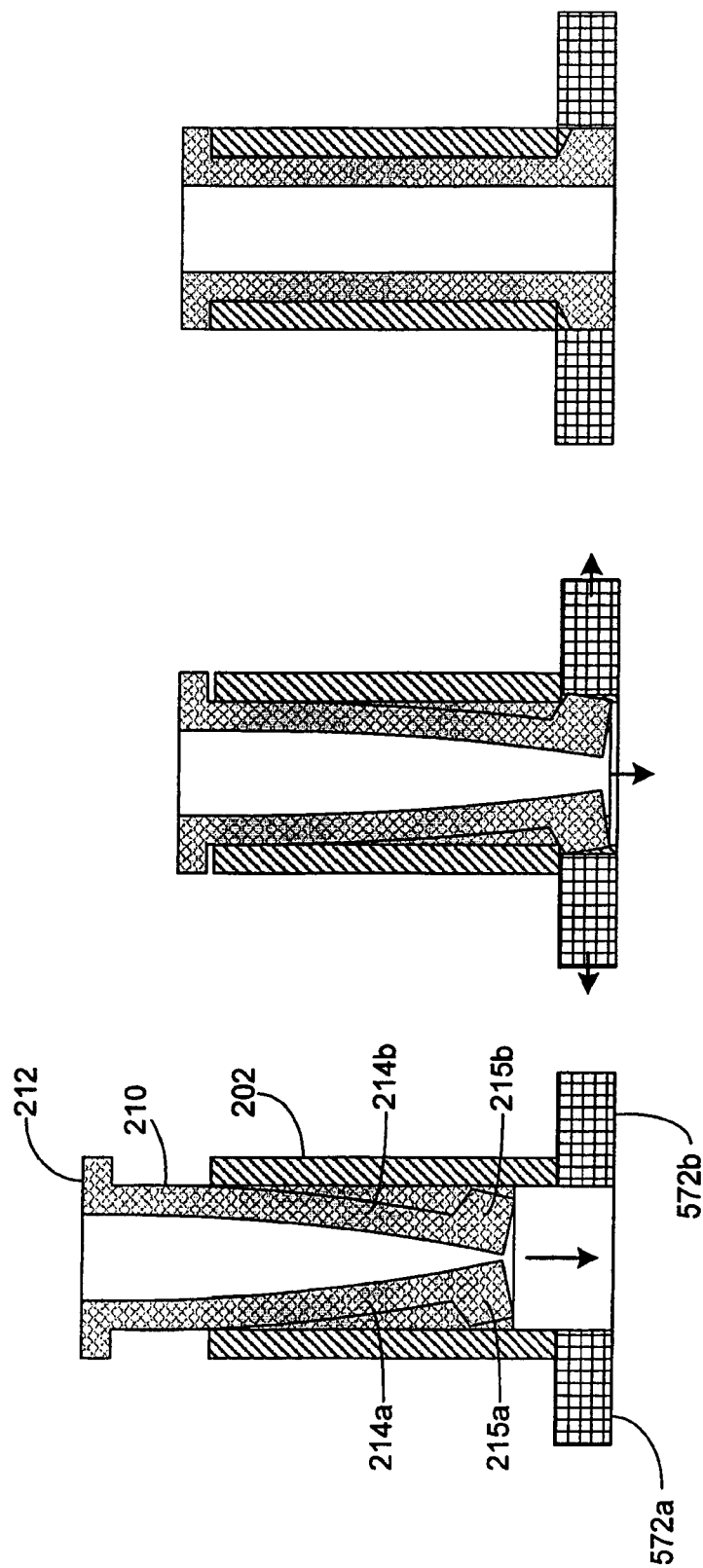
FIG. 10 illustrate exemplary downward movement of an inner sleeve having a pair of opposing tongue members, the tongue member protrusions extending therethrough a pair of opposing notches of the outer sleeve and pushing out retention members as the inner sleeve is lowered from a first raised position (shown on the left), through an intermediate position (middle), to a second lowered position (shown on the right).

In one aspect, when the protrusion fully extends into the opening, such as when the inner sleeve is in the second position, the tongue member extends longitudinally at an angle substantially parallel to the longitudinal axis of the tongue member. In a further aspect, the protrusion can comprise an upper surface and an opposing lower surface separated therefrom the upper surface by a front surface of the protrusion. As illustrated in FIG. 9, in one aspect, the upper surface can taper downwardly toward the front surface of the protrusion so that as the inner sleeve is moved from the first to the second position, the protrusion can progressively ease into the notch 104.

Figure 11:
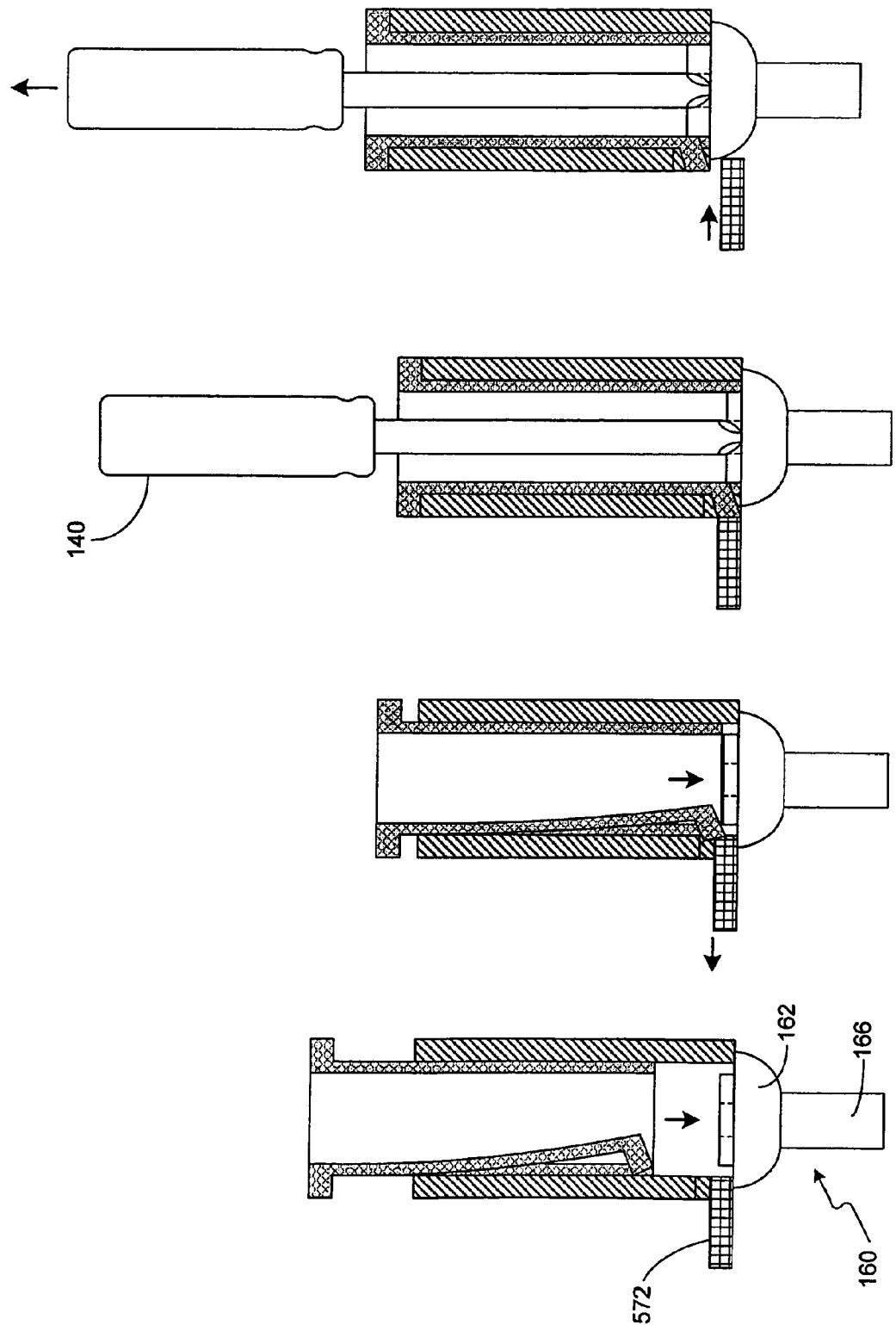
FIG. 11 illustrate exemplary downward movement of an inner sleeve within an outer sleeve, the tongue member protrusion of the inner sleeve extending therethrough the notch of the outer sleeve and pushing out a retention member, and the removal of a bone screw with a removal tool.
Figure 12:
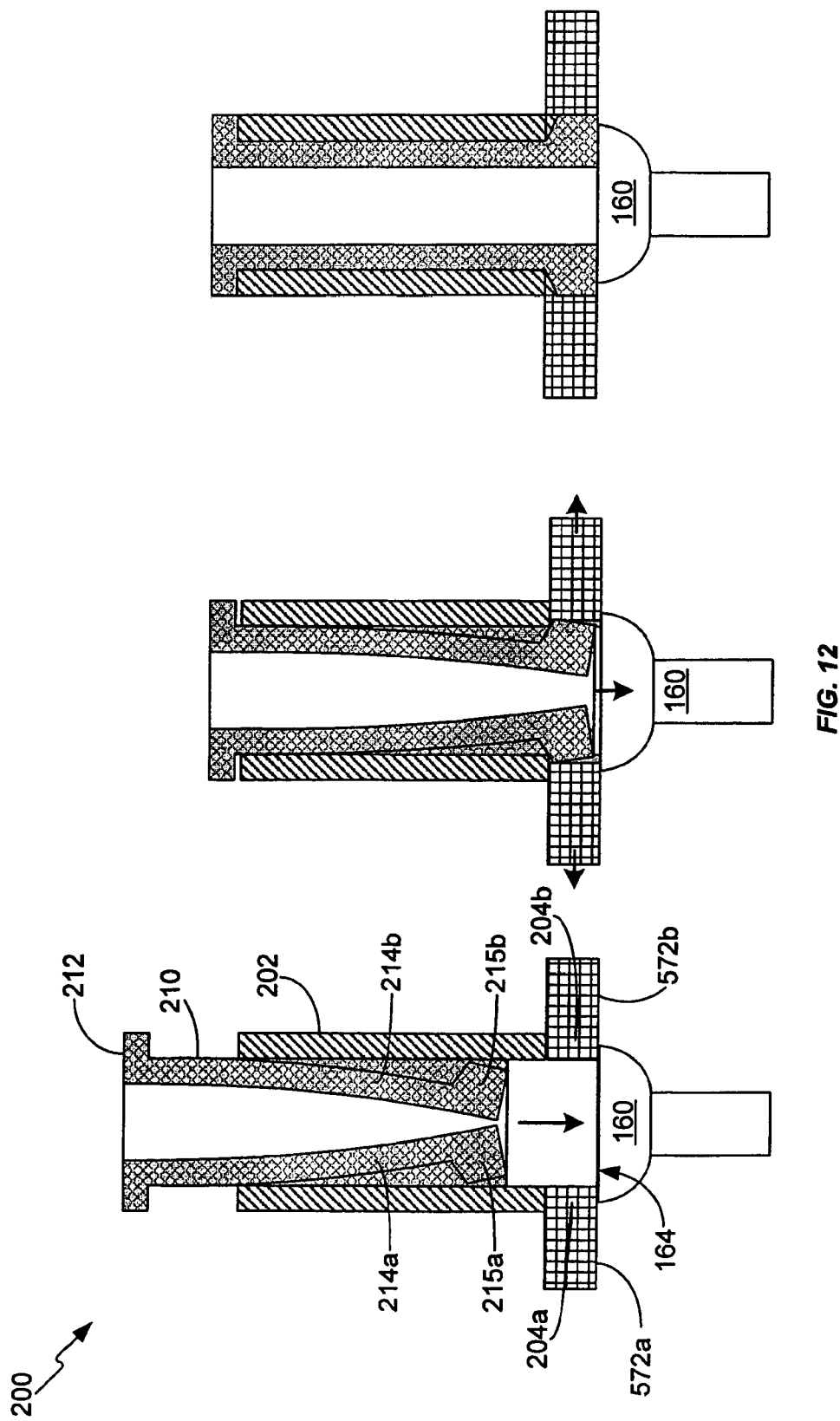
FIG. 12 are side cross-sectional view of a bone screw removal device being used to remove a bone screw retained by a rectangular retention member.

As illustrated in FIGS. 9-12, in use, an exemplary bone screw removal device can be used to remove a bone screw from a bone retention system. A removal device can be placed within a bore 154 of an exemplary bone screw retention system until the lower surface of the outer sleeve substantially abuts or rests on the shoulder 164 of the bone screw 160 positioned therein the bore. It is contemplated that when the outer sleeve is positioned within the bore, the inner sleeve is in a first position in which the flange 112 is spaced from the upper edge of the outer sleeve. The outer sleeve can be positioned within the bore such that an opening or notch 104 of the outer sleeve is positioned over a retention member of the bone screw retention system. Thus, the respective retention member may extend into the inner portion (i.e., the conduit) of the outer sleeve via the respective notch. For example, as shown in FIG. 12, an exemplary bone screw removal device 200 can be used to remove a bone screw 160 retained by a rectangular retention member 572. The bone screw removal device, thus, can have a pair of opposing notches 204a and 204b extending upwardly from the lower surface of the outer sleeve.

The removal device can be positioned within the bore such that each of the openings 204a and 204b is positioned over a respective side of the rectangular retention member 572a and 572b. It is contemplated that the openings can be sized and shaped to receive the retention members. As shown in FIG. 12, when the outer sleeve is positioned therein the bore, the retention members extend inwardly toward the inner conduit of the outer sleeve. After the outer sleeve is positioned within the bore, the inner sleeve can be moved from the first position to a second position in which the flange substantially abuts the upper edge of the outer sleeve. As the inner sleeve is moved toward the second position, each of the protrusions 215a and 215b can extend into the respective openings 204a and 204b. As described above, the upper surfaces of the protrusions may taper downwardly toward the front surfaces of the protrusions, such that the protrusions can progressively ease into the openings as the inner sleeve is lowered. As the protrusions enter the openings, the front surfaces can engage the respective retention members. As can be appreciated, in one embodiment, if the spring constant $K_T$ of the tongue members is greater than the spring constant $K_R$ of the retention members, as the inner sleeve is moved completely to the second position, as shown in FIG. 12, the retention members will be laterally pushed outwardly away from the longitudinal axis of the bore by the protrusions, to a position in which they no longer cover or retain the bone screw. The progression of the inner sleeve from the first position to the second position is also illustrated in FIG. 11.

Figure 13:
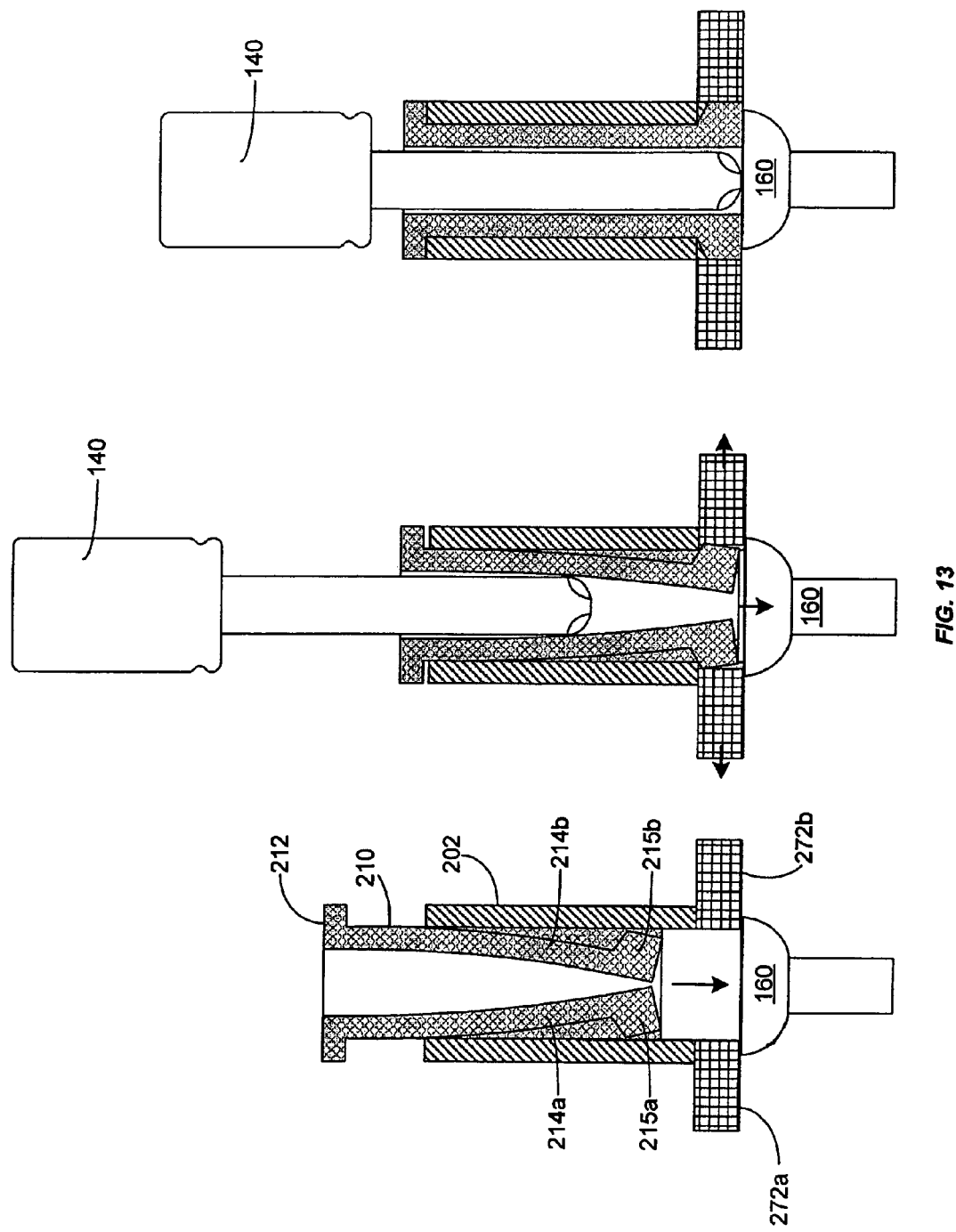
FIG. 13 illustrate exemplary use of a removal tool to push out at least one tongue member, thereby pushing out at least one retention member.

In another embodiment, a removal tool 140 can be inserted into the removal device via the conduit of the inner sleeve. Exemplary removal tools can comprise screwdrivers having a head that mates with a portion of the head of the bone screw, or other tools known in the art. In one aspect, a removal tool can be configured to engage the at least one tongue member, thereby urging the protrusion of the at least one tongue member laterally outwardly away from the longitudinal axis of the bore, such as shown in FIG. 13. Thus, even if the spring constant $K_T$ of the at least one tongue member is not greater than the spring constant $K_R$ of the at least one retention member, a distal portion of the removal tool can engage the at least one tongue member and push at least one tongue member, and therefore, the at least one protrusion laterally outwardly away from the longitudinal axis of the bore, which also pushes the at least one retention member laterally outwardly away from the longitudinal axis of the bore to a position in which the at least one retention member no longer covers or retains the bone screw.

With the inner sleeve in the second position (and with the retention member(s) no longer retaining the bone screw), the physician or surgeon can use the removal tool to unscrew the bone screw and thus remove it from the bore. As shown in FIG. 11 (far right), as the bone screw is removed from the bore, it moves upward. Because the outer sleeve rests on a portion of the shoulder 164, as the bone screw moves upwardly, the removal device moves upwardly. Due to the tapered shape of the head of the bone screw, the retention member can slide or ease into its relaxed, unflexed position as the bone screw is removed. After use, the bone screw removal device can be reused. A physician can manually press the protrusion(s) inwardly and then slightly upwardly so that the inner sleeve can be returned to its first position.

FIGS. 14A-14D illustrate another exemplary bone screw removal device 300. The bone screw removal device can comprise a main sleeve 302 that is substantially cylindrical and defines a conduit therein. In a further aspect, the main sleeve has an upper surface and an opposing lower surface. The main sleeve can define one or more openings 304 extending upwardly from the lower surface of the main sleeve. The removal device 300 can further comprise a removal sleeve 320 comprising a band portion 322 that is substantially cylindrical and has a diameter greater than a diameter of the main sleeve 302. The removal sleeve can further comprise a tongue member 324 that extends downwardly from the band portion. As shown in FIG. 14C, in one aspect, in its resting (i.e., unstressed) position the tongue member extends downwardly from the band portion at an angle that is less than 90°. For example, the tongue member can be at an angle of between 45° and 90°. In a further aspect, the tongue member can be at an angle of between 75° and 90°, such as 85°. The removal sleeve 320 can be positioned around the main sleeve 302 with the tongue member 324 extending downwardly over the opening 304. In this position, the tongue member can extend inwardly into the main sleeve via the opening, such as shown in FIG. 14C (resting position).

In a further aspect, the removal sleeve can be removably attached to the main sleeve. For example, in one aspect, one or more indentations can be formed within the exterior surface of the main sleeve. The band portion of the removal sleeve can have protrusions extending inwardly from its inner surface. The protrusions can be sized, shaped and positioned to be received by the indentations of the main sleeve when the removal sleeve is placed around the main sleeve. Thus, the removal sleeve can snap into a desired position for use. In a further aspect, the indentation(s) can be substantially round, such as, without limitation, hemispherical, partially spherical, etc. The protrusion(s) can be similarly shaped to be received by the indentation.

Optionally, a circumferential groove can be formed on the main sleeve that can be sized and shaped to receive the band portion of the removal sleeve. Thus, the groove can have a height that is slightly greater than the height of the band portion, and can have a predetermined depth sufficient to receive the band portion and substantially prevent it from moving (i.e., up or down) when it is in use. In another aspect, a plurality of circumferential flanges can be formed on the main sleeve. The flanges can be spaced at a predetermined distance from each other along the main sleeve such that the band portion of the removal sleeve can be received and secured therebetween. In yet another aspect, the removal sleeve can be fixedly attached to the main sleeve in a predetermined position.

The bone screw removal device 300 can be used by a physician to remove a bone screw from a bone screw retention system. The main sleeve 302 can be positioned within a bore, such that the main sleeve rests on the shoulder of the bone screw. As described above, the main sleeve can be positioned therein the bore such that the opening or notch 304 is positioned over a respective retention member, allowing the retention member to extend inwardly into the main sleeve via the opening. A removal tool can be inserted into the conduit of the main sleeve to remove the bone screw. As the tool is inserted therein the main sleeve, it is contemplated that it can contact the tongue member and thus force the tongue member to its in-use position (FIG. 14D). As the tongue member is forced or moved to its in-use position, it will consequently move the respective retention member to a position in which it no longer obstructs or retains the bone screw, and the bone screw can be removed. It is contemplated that the exemplary bone screw removal device 300 can comprise more than one opening, and more than one tongue member, such that multiple retention members of the bone screw retention system can substantially simultaneously be moved to non-retaining positions.

According to various aspects, various components of a bone screw retention system and bone screw removal device can be formed from a biocompatible, flexible material such as, but not limited to, shape-memory alloys, titanium alloy and the like as disclosed in U.S. Pat. Nos. 4,857,269 and 4,952,236, which are incorporated in their entirety herein by reference. Further, polymeric materials such as, for example, ultra-high molecular weight polyethylene can also be used to form various components of the bone screw retention and removal system. Such exemplary materials can be used, for example, to form the exemplary retention members described above. The materials can also be used to form the tongue members of the various bone screw removal devices described above. In yet another aspect, such materials can be used to form all of the components of the exemplary bone screw removal devices described above.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein.

What is claimed is:

1. A bone screw retention system for retaining bone screws therein, and releasing bone screws therefrom, a plate that defines a plurality of transversely extending bores configured for receiving bone screws and a retention member cavity corresponding to each bore, the retaining system comprising:

an elastically deformable retention member having an edge portion, wherein at least a portion of the retention member is positioned therein each at least one cavity such that portions of the at least one retention member extend into an upper region of each of the bores, wherein the retention member is configured to mount therein the at least one cavity and is movable between a first relaxed position and a second compressed position, wherein, in the first relaxed position, a portion of the edge portion of the retention member extends inwardly substantially transverse to and toward the longitudinal axis of the respective bore and into the upper region of the bore, which decreases an effective inner diameter of the upper region of the bore, and wherein, in the second compressed position, portions of the retention member are medially biased outwardly away from the longitudinal axis of the bore towards an outer wall of the upper region of the bore, which increases the effective inner diameter of the upper region of the bore, and wherein in the first relaxed position, the retention member is a continuous closed loop.

2. The bone screw retention system of claim 1, wherein, in the first relaxed position, the retention member is substantially circular in shape.

3. The bone screw retention system of claim 1, wherein, in the first relaxed position, the retention member is substantially oval in shape.

4. The bone screw retention system of claim 1, wherein, in the first relaxed position, the retention member is substantially elliptical in shape.

5. The bone screw retention system of claim 1, wherein, in the first relaxed position, the retention member is substantially rectangular in shape.

6. The bone screw retention system of claim 1, wherein, in the first relaxed position, the retention member is substantially square in shape.

7. The bone screw retention system of claim 1, wherein the elastically deformable retention member comprises a plurality of elastically deformable retention members.

8. The bone screw retention system of claim 7, wherein the elastically deformable retention member is positioned therein each at least one cavity such that a center of the retention member is substantially in the same position when the at least one retention member is in the first relaxed position and the second compressed position.

9. The bone screw removal system of claim 1, further comprising a means for engaging portions of the edge portion of the retention member thereby medially biasing portions of the retention member away from the longitudinal axis of the bore towards an outer wall of the upper region of the bore increasing the effective inner diameter of the upper region of the bore.

10. The bone screw retention system of claim 1, further comprising a bone screw removal system comprising:
  a bone screw removal tool;
  an inner tubular sleeve having an outer diameter and defining a conduit extending from an upper end to a lower end of the inner sleeve, wherein the inner sleeve has at least one resilient tongue member comprising at least one protrusion extending outwardly from the lower end of the inner sleeve; and
  an outer tubular sleeve having an inner diameter and defining at least one notch in a lower end of the outer sleeve for complementarily receiving the at least one protrusion of the inner sleeve;
  wherein the inner diameter of the outer sleeve is greater than the outer diameter of the inner sleeve, wherein when the inner sleeve is inserted into the outer sleeve, the at least one tongue member is movable about and between a first, compressed position, in which the at least one protrusion of the at least one tongue member is resiliently biased inwardly toward the longitudinal axis of the conduit of the inner sleeve, and a second relaxed position, in which the at least one protrusion of the at least one tongue member of the inner sleeve is complementarily received therein the at least one notch of the outer sleeve.

11. The bone screw retention system of claim 10, wherein in the second relaxed position of the tongue member, the at least one protrusion engages an outer edge of the edge portion of the retention member.

12. The bone screw retention system of claim 10, wherein in the second relaxed position of the tongue member, the at least one protrusion engages an inner edge of the edge portion of the retention member.

13. The bone screw removal system of claim 10, wherein the at least one resilient tongue member comprises a pair of resilient tongue members.

14. The bone screw removal system of claim 10, wherein the at least one resilient tongue members comprises a plurality of resilient tongue members.

15. The bone screw removal system of claim 10, wherein the at least one resilient tongue member has a spring constant greater than the spring constant of the at least one retaining member.

16. The bone screw removal system of claim 10, wherein a portion of a distal end of the bone screw removal tool is configured to operatively engage a head of the bone screw.

17. The bone screw removal system of claim 10, wherein a portion of a distal end of the bone screw removal tool is configured to engage at least a portion of the at least one protrusion of the at least one resilient tongue members, thereby urging the protrusion outwardly away from the longitudinal axis of the respective bore.

18. The bone screw removal system of claim 10, wherein the at least one protrusion of the at least one resilient tongue members is configured to be in opposition to the retention member.

19. The bone screw removal system of claim 10, wherein an inner diameter of the conduit of the inner sleeve member is greater than the diameter of a head of the bone screw.

20. The bone screw removal system of claim 10, wherein, in the second relaxed position, the at least one protrusion of the at least one resilient tongue member engages portions of the edge portion of the retention member thereby medially biasing portions of the retention member away from the longitudinal axis of the bore towards an outer wall of the upper region of the bore increasing the effective inner diameter of the upper region of the bore.

21. The bone screw removal system of claim 10, wherein, in the second relaxed position, an outer surface of the at least one protrusion of the at least one resilient tongue member is at least co-planar with an exterior surface proximate the at least one notch defined therein the outer tubular sleeve.

22. A bone screw retention system comprising:
  a plate that defines a plurality of transversely extending bores configured for receiving bone screws and a retention member cavity corresponding to each bore;
  an elastically deformable retention member having an edge portion, wherein at least a portion of the retention member is positioned therein each cavity such that portions of the retention member extend into an upper region of each of the bores, wherein the retention member is configured to mount therein the cavity and is movable between a first relaxed position and a second compressed position, wherein, in the first relaxed position, at least a portion of the retention member extends inwardly substantially transverse to and toward the longitudinal axis of the respective bore and into the upper region of the bore which decreases an effective inner diameter of the upper region of the bore, and wherein, in the second compressed position, portions of the retention member are medially biased outwardly away from the longitudinal axis of the bore towards an outer wall of the upper region of the bore, which increases the effective inner diameter of the upper region of the bore, and wherein the retention member is a continuous closed loop; and a bone screw removal system.

23. The bone screw retention system of claim 22, wherein the bone screw removal system comprises:

a bone screw removal tool;

an inner tubular sleeve having an outer diameter and defining a conduit extending from an upper end to a lower end of the inner sleeve, wherein the inner sleeve has at least one resilient tongue member comprising at least one protrusion extending outwardly from the lower end of the inner sleeve; and an outer tubular sleeve having an inner diameter and defining at least one notch in a lower end of the outer sleeve for receiving the at least one protrusion of the inner sleeve;

wherein the inner diameter of the outer sleeve is greater than the outer diameter of the inner sleeve, wherein when the inner sleeve is inserted into the outer sleeve, the at least one protrusion is movable about and between a first, compressed position, in which the protrusion of the at least one tongue member is resiliently biased inward toward the center of the conduit of the inner sleeve, and a second relaxed position, in which the protrusion of the at least one tongue member of the inner sleeve is received therein the at least one notch of the outer sleeve outwardly from the center of the conduit of the inner sleeve.

* * * * *